US012622990B2

(12) United States Patent     (10) Patent No.:   US 12,622,990 B2

Sivertsen et al.     (45) Date of Patent:    May 12, 2026

(54) STERILIZATION OF TESTING EQUIPMENT

(71) Applicant: Assaya LLC, Roswell, GA (US)

(72) Inventors: Clas Sivertsen, Lilburn, GA (US); Tom Sivertsen, Kristiansund (NO); Roy Larsen, Kristiansund (NO); Sturla Sivertsen, Kristiansund (NO)

(73) Assignee: Assaya LLC, Lakeside, MT (US)

( * ) Notice: Subject to any disclaimer, the term of this patent is extended or adjusted under 35 U.S.C. 154(b) by 101 days.

(21) Appl. No.: 17/359,302

(22) Filed: Jun. 25, 2021

(65) Prior Publication Data

US 2024/0424160 A1     Dec. 26, 2024

(51) Int. Cl.

| | |
|---|---|
| *A61L 2/24* | (2006.01) |
| *A61L 2/10* | (2006.01) |
| *A61L 2/26* | (2006.01) |
| *G06K 7/14* | (2006.01) |

(52) U.S. Cl.
CPC ...... *A61L 2/24* (2013.01); *A61L 2/10* (2013.01); *A61L 2/26* (2013.01); *A61L 2202/11* (2013.01); *A61L 2202/14* (2013.01); *G06K 7/1417* (2013.01)

(58) Field of Classification Search
CPC ..................................... A61L 2/10; A61L 2/24
See application file for complete search history.

(56) References Cited

U.S. PATENT DOCUMENTS

| | | | |
|---|---|---|---|
| 5,075,078 | A | 12/1991 | Osikowicz et al. |
| 5,308,775 | A | 5/1994 | Donovan et al. |
| 5,717,778 | A | 2/1998 | Chu et al. |
| 5,875,258 | A | 2/1999 | Ortyn et al. |
| 5,968,839 | A | 10/1999 | Blatt et al. |
| 6,061,128 | A | 5/2000 | Zweig et al. |
| 6,267,722 | B1 | 7/2001 | Anderson et al. |
| 6,394,952 | B1 | 5/2002 | Anderson et al. |
| 6,664,071 | B1 | 12/2003 | Windhab et al. |
| 7,177,235 | B2 | 2/2007 | Rund |
| 7,236,428 | B1 | 6/2007 | Morse |
| 7,267,799 | B1 | 9/2007 | Borich et al. |
| 9,702,872 | B1 | 7/2017 | Wang et al. |

(Continued)

FOREIGN PATENT DOCUMENTS

| | | | |
|---|---|---|---|
| CN | 102482702 A | 5/2012 | |
| CN | 102539735 A | 7/2012 | |

(Continued)

OTHER PUBLICATIONS

Anfossi et al., Multiplex Lateral Flow Immunoassay: An Overview of Strategies towards High-throughput Point-of-Need Testing, Biosensors (Basel). Mar. 2019; 9(1): 2. (Year: 2018).

(Continued)

*Primary Examiner* — Donald R Spamer
*Assistant Examiner* — Kayla Rose Sarantakos
(74) *Attorney, Agent, or Firm* — Nicholson De Vos Webster & Elliott LLP; Judith Szepesi

(57) ABSTRACT

A system including a processor and memory coupled to the processor. The system also includes a lateral flow assay ("LFA") strip reader coupled to the processor for transmitting an LFA strip image to the processor. The processor initiates a sterilization process when the LFA strip image includes a visual feature indicating a sterilization trigger.

26 Claims, 24 Drawing Sheets

(56)                    References Cited

U.S. PATENT DOCUMENTS

| | | | |
|---|---|---|---|
| 9,857,372 | B1 | 1/2018 | Pulitzer et al. |
| 9,857,373 | B1 | 1/2018 | Pulitzer et al. |
| 10,197,558 | B1 | 2/2019 | Saaski et al. |
| 10,823,746 | B1 | 11/2020 | Busa et al. |
| 11,740,203 | B2 * | 8/2023 | Galen .................... G01N 33/68 |
| | | | 204/603 |
| 11,802,868 | B2 | 10/2023 | Pulitzer et al. |
| 12,094,603 | B2 | 9/2024 | Sivertsen |
| 12,311,065 | B1 * | 5/2025 | Miller ....................... A61L 2/10 |
| 2001/0053336 | A1 | 12/2001 | Hammer et al. |
| 2003/0021726 | A1 | 1/2003 | Wu et al. |
| 2003/0040128 | A1 | 2/2003 | Meador et al. |
| 2003/0120633 | A1 | 6/2003 | Torre-Bueno |
| 2003/0139903 | A1 | 7/2003 | Zweig et al. |
| 2003/0143530 | A1 | 7/2003 | Klepp et al. |
| 2004/0122790 | A1 | 6/2004 | Walker et al. |
| 2005/0008538 | A1 | 1/2005 | Anderson et al. |
| 2005/0203353 | A1 | 9/2005 | Ma et al. |
| 2005/0255001 | A1 | 11/2005 | Padmanabhan et al. |
| 2005/0255600 | A1 | 11/2005 | Padmanabhan et al. |
| 2006/0216832 | A1 | 9/2006 | Nishikawa et al. |
| 2006/0223192 | A1 | 10/2006 | Smith et al. |
| 2006/0246599 | A1 | 11/2006 | Rosenstein et al. |
| 2006/0274145 | A1 | 12/2006 | Reiner |
| 2006/0292040 | A1 | 12/2006 | Wickstead et al. |
| 2007/0122914 | A1 | 5/2007 | Curry |
| 2007/0143035 | A1 | 6/2007 | Petruno |
| 2008/0186499 | A1 | 8/2008 | Krauth |
| 2009/0061450 | A1 | 3/2009 | Hunter |
| 2009/0074282 | A1 | 3/2009 | Pinard et al. |
| 2009/0087926 | A1 | 4/2009 | Hasegawa et al. |
| 2009/0155811 | A1 | 6/2009 | Natan et al. |
| 2009/0312663 | A1 | 12/2009 | John et al. |
| 2010/0045789 | A1 | 2/2010 | Fleming et al. |
| 2010/0099115 | A1 | 4/2010 | Mach et al. |
| 2010/0105024 | A1 | 4/2010 | Xu et al. |
| 2010/0135857 | A1 | 6/2010 | Hunter et al. |
| 2010/0267049 | A1 | 10/2010 | Rutter et al. |
| 2010/0331651 | A1 | 12/2010 | Groll |
| 2011/0213564 | A1 | 9/2011 | Henke |
| 2011/0213579 | A1 | 9/2011 | Henke |
| 2012/0071342 | A1 | 3/2012 | Lochhead et al. |
| 2012/0115214 | A1 | 5/2012 | Battrell et al. |
| 2012/0122236 | A1 | 5/2012 | Tarpey |
| 2012/0123686 | A1 | 5/2012 | Xiang et al. |
| 2012/0281970 | A1 | 11/2012 | Garibaldi et al. |
| 2012/0282154 | A1 | 11/2012 | Slowey et al. |
| 2013/0203043 | A1 | 8/2013 | Ozcan et al. |
| 2013/0273645 | A1 | 10/2013 | Waga |
| 2013/0288254 | A1 | 10/2013 | Pollack et al. |
| 2013/0338243 | A1 | 12/2013 | Kentsis et al. |
| 2014/0017812 | A1 | 1/2014 | Smith et al. |
| 2014/0018779 | A1 | 1/2014 | Worrell et al. |
| 2014/0154792 | A1 | 6/2014 | Moynihan et al. |
| 2014/0227681 | A1 | 8/2014 | Fleming et al. |
| 2014/0278832 | A1 | 9/2014 | Glavina et al. |
| 2014/0324373 | A1 | 10/2014 | Xiang et al. |
| 2014/0339100 | A1 | 11/2014 | Malecha |
| 2015/0010992 | A1 | 1/2015 | Fleming et al. |
| 2015/0099306 | A1 | 4/2015 | Ku |
| 2015/0244852 | A1 | 8/2015 | Erickson et al. |
| 2015/0338387 | A1 | 11/2015 | Ehrenkranz |
| 2015/0350605 | A1 | 12/2015 | Price et al. |
| 2016/0030613 | A1 | 2/2016 | Paul et al. |
| 2016/0085913 | A1 | 3/2016 | Evans et al. |
| 2016/0131645 | A1 | 5/2016 | Wang |
| 2016/0157598 | A1 | 6/2016 | Anelevitz |
| 2016/0178607 | A1 | 6/2016 | Husheer et al. |
| 2016/0188937 | A1 | 6/2016 | Tyrrell et al. |
| 2016/0265032 | A1 | 9/2016 | Sethi et al. |
| 2016/0356800 | A1 | 12/2016 | Glavina et al. |
| 2016/0356801 | A1 | 12/2016 | Glavina et al. |
| 2016/0370366 | A1 | 12/2016 | Fleming et al. |
| 2017/0049915 | A1 * | 2/2017 | Brais .................... H05B 47/115 |
| 2017/0160258 | A1 | 6/2017 | Hengstler et al. |

| | | | |
|---|---|---|---|
| 2017/0184586 | A1 | 6/2017 | Hopper |
| 2018/0031551 | A1 | 2/2018 | Karlovac et al. |
| 2018/0071741 | A1 | 3/2018 | Kelly et al. |
| 2018/0106789 | A1 | 4/2018 | Pulitzer et al. |
| 2018/0107790 | A1 | 4/2018 | Pulitzer et al. |
| 2018/0149600 | A1 | 5/2018 | Farrell |
| 2018/0164222 | A1 | 6/2018 | Pulitzer et al. |
| 2018/0246038 | A1 | 8/2018 | Hunter |
| 2018/0259449 | A1 | 9/2018 | Poulsen et al. |
| 2018/0293350 | A1 | 10/2018 | Dimov et al. |
| 2018/0348198 | A1 | 12/2018 | Broadwell |
| 2018/0372734 | A1 | 12/2018 | Pfenninger et al. |
| 2019/0070324 | A1 * | 3/2019 | Hardin .................... A61L 2/084 |
| 2019/0096516 | A1 | 3/2019 | Pulitzer et al. |
| 2019/0122768 | A1 | 4/2019 | Pulitzer et al. |
| 2019/0224685 | A1 | 7/2019 | Benenati |
| 2019/0229907 | A1 | 7/2019 | Nicolson et al. |
| 2019/0267822 | A1 | 8/2019 | Voit et al. |
| 2019/0317115 | A1 | 10/2019 | Maclean et al. |
| 2019/0339264 | A1 | 11/2019 | Gary et al. |
| 2019/0369094 | A1 | 12/2019 | Ishikawa et al. |
| 2020/0330979 | A1 | 10/2020 | Cyr et al. |
| 2020/0386753 | A1 | 12/2020 | Somes et al. |
| 2020/0408715 | A1 | 12/2020 | Galen et al. |
| 2021/0086177 | A1 | 3/2021 | Lin |
| 2021/0132035 | A1 | 5/2021 | Adelman |
| 2021/0172945 | A1 | 6/2021 | Armbruster et al. |
| 2021/0263018 | A1 | 8/2021 | Taran |
| 2021/0293688 | A1 | 9/2021 | Chang et al. |
| 2021/0319911 | A1 | 10/2021 | Hall et al. |
| 2021/0327056 | A1 | 10/2021 | Needham et al. |
| 2021/0389233 | A1 | 12/2021 | Hatamian |
| 2022/0055036 | A1 | 2/2022 | Tycon |
| 2022/0091114 | A1 | 3/2022 | Levin et al. |
| 2022/0178920 | A1 | 6/2022 | Howard |
| 2022/0254027 | A1 | 8/2022 | Lin et al. |
| 2022/0254133 | A1 | 8/2022 | Adsul et al. |
| 2022/0258155 | A1 | 8/2022 | Ren et al. |
| 2022/0296755 | A1 * | 9/2022 | Wurmfeld ............ G06K 7/1413 |
| 2022/0304560 | A1 | 9/2022 | Jackson et al. |
| 2022/0399109 | A1 | 12/2022 | Sivertsen |
| 2022/0404354 | A1 * | 12/2022 | Robinson ........... G01N 21/8483 |
| 2022/0405551 | A1 | 12/2022 | Jain et al. |
| 2022/0412961 | A1 | 12/2022 | Jolly et al. |
| 2023/0213452 | A1 | 7/2023 | Minobe et al. |
| 2023/0274538 | A1 | 8/2023 | Sia et al. |
| 2023/0351754 | A1 | 11/2023 | Satish et al. |
| 2024/0363206 | A1 | 10/2024 | Mayer |
| 2024/0387010 | A1 | 11/2024 | Sivertsen et al. |
| 2024/0402198 | A1 | 12/2024 | Sivertsen |
| 2024/0404658 | A1 | 12/2024 | Sivertsen et al. |
| 2024/0412829 | A1 | 12/2024 | Sivertsen et al. |
| 2024/0424160 | A1 | 12/2024 | Sivertsen et al. |
| 2024/0428905 | A1 | 12/2024 | Sivertsen |

FOREIGN PATENT DOCUMENTS

| | | | |
|---|---|---|---|
| CN | 106680496 A | | 5/2017 |
| CN | 211086092 U | * | 7/2020 |
| EP | 0480208 A2 | | 4/1992 |
| EP | 2839264 A1 | | 2/2015 |
| TW | 201833554 A | | 9/2018 |
| TW | M588797 U | | 1/2020 |
| WO | 2013/119266 A1 | | 8/2013 |
| WO | 2013/158504 A1 | | 10/2013 |
| WO | 2020/174895 A1 | | 9/2020 |
| WO | 2020/251460 A1 | | 12/2020 |

OTHER PUBLICATIONS

AssayGenie, Rapid covid19 antibody detection test principles and methods, published: 2020, https://www.assaygenie.com/rapid-covid 19-antibody-detection-tests-principles-and-methods (Year: 2020).

Azzi et al, Rapid Salivary Test suitable for a mass screening program to detect SARS-CoV-2: A diagnostic accuracy study, Journal of Infection, vol. 81, Issue 3, Sep. 2020, pp. e75-e78 (Year: 2020).

(56)                    References Cited

OTHER PUBLICATIONS

Badi et al., The Effect of Gold Salt Concentration in the Production of Gold Nanospheres, Jan. 2020, Journal of Applied Mathematics and Physics (Year: 2020).

Baker et al., The SARS-COV-2 Spike Protein Binds Sialic Acids and Enables Rapid Detection in a Lateral Flow Point of Care Diagnostic Device, 2020, vol. 6, 2046-2052 (Year: 2020).

Contreras-Aguilar, Changes in Saliva Analytes in Dairy Cows during Peripartum: A Pilot Study, Mar. 9, 2021, Animals, vol. 11, issues 3 (Year: 2021).

Independent Forensics, Developmental Validation of RSID-Urine, Mar. 2021, Independent Forensics, https://www.ifi-test.com/rsid-urine/ (Year: 2021).

Larsen et al., Fluorometric determination of uric acid in bovine milk, 2010, Journal of Dairy Research, vol. 77, 438-444 (Year: 2010).

Old et al., Developmental Validation of RSIDTM-Saliva: A Lateral Flow Immunochromatographic Strip Test for the Forensic Detection of Saliva, J Forensic Sci, Jul. 2009, vol. 54, No. 4 (Year: 2009).

Richardson et al., Amylase in Cow's Milk, 1936, Journal of Dairy Science, vol. 19, Issue 12, 761-772 (Year: 1936).

StatTechnologies, Adulteration Test Strips, 2017, StatTechnologies, https://stat-technologies.com/product/adulteration-test-strips/ (Year: 2017).

Stuart Patton, Some Practical Implications of the Milk Mucins, 1999, Journal of Dairy Science, vol. 82, Issue 6, 1115-1117 (Year:1999).

Thao et al. (American Clinical Society, 2017, p. 6781-6786).

Urusov AE et al. (2019) Towards Lateral Flow Quantitative Assays: Detection Approaches. Biosensors, 9(3), 16 pgs; https://doi.org/10.3390/bios9030089 (Year: 2019).

Zhou et al. Paper electrode integrated lateral flow immunosensor for quantitative analysis of oxidative stress induced DNA damage, 2014, Analyst, 139(11), 2850-2857 (Year: 2014).

Correa, M. E. et al, Pregnancy Hypertension: An International Journal of Women's Cardiovascular Health 2017, 750-53. (Year: 2017).

De Silva, D. A. et al, Journal of Obstetrics and Gynaecology Canada 2014, 36, 605-612. (Year: 2014).

Filippini, D. et al, Analyst 2006, 131, 111-117. (Year: 2006).

Hou, Y. et al., Nanoscale Research Letters 2017, 12, paper 291, 13 pages. (Year: 2017).

Lin, C.-S. et al, Optik 2004, 115, 363-369. (Year: 2004).

Magiati, M. et al, Microchimica Acta 2018, 185, paper 314, 9 pages. (Year: 2018).

O'Farrell, B., in Lateral Flow Immunoassay 2009, Wong, R. C. et al. (eds.), Humana Press, New York, 1-33. (Year: 2009).

Panic, G. et al, Parasites & Vectors 2019, 12, paper 298, 7 pages. (Year: 2019).

Tucker, K. et al, Pregnancy Hypertension 2018, 12, 161-168. (Year: 2018).

Waters, L. C. et al, Journal of Hazardous Materials 1995, 43, 1-12. (Year: 1995).

Waugh, J. J. S. et al, BJOG: an International Journal of Obstetrics and Gynaecology 2005, 112, 412-417. (Year: 2005).

Xu, Y. et al., Analytical Chemistry 2018, 90, 708-715 with 13 pages of supporting information. (Year: 2018).

Grant et al. (May 7, 2020, Intellectual Ventures Lab, p. 1-11).

* cited by examiner

120b

UVC 60 SEC STERILIZA
DO NOT WATCH DURING OPE
SEVERE EYE DAMAGE MA

120b

STERILIZATION OF TESTING EQUIPMENT

BACKGROUND

The present invention generally relates to sterilization and more specifically, to a testing equipment sterilization system and method.

Testing devices receive a number of test samples throughout the course of a day. These test samples may contain viruses, bacteria, and contaminants. Present day testing systems often lack sterilization features within the equipment. Those that do have sterilization systems in place lack adequate controls and triggering means.

SUMMARY

Embodiments of the present invention are directed to a system including a processor and memory coupled to the processor. The system also includes a lateral flow assay ("LFA") strip reader coupled to the processor for transmitting an LFA strip image to the processor. The processor initiates a sterilization process when the LFA strip image includes a visual feature indicating a sterilization trigger.

Further embodiments are directed to a method that reads a lateral flow assay strip, using an imaging device, to generate an LFA strip image. The method provides the LFA strip image to a processor and activates, using the processor, a sterilization process when the LFA strip image contains a visual feature intended to trigger the sterilization process.

Further embodiments of the present invention are directed to a method. The method builds an equivalence curve for a lateral flow assay ("LFA") strip. The method receives, by a processor, test information for the LFA strip and receives, by the processor, an image of the LFA strip. The method receives, by the processor, a known concentration of a viral load placed onto the LFA strip and associates, by the processor, an intensity of a portion of the image of the cassette with the known concentration of the viral load placed onto the LFA strip and a standardized value. The method repeats one or more of the previous steps, by the processor, until the equivalence curve is created and stores, by the processor, the equivalence curve.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
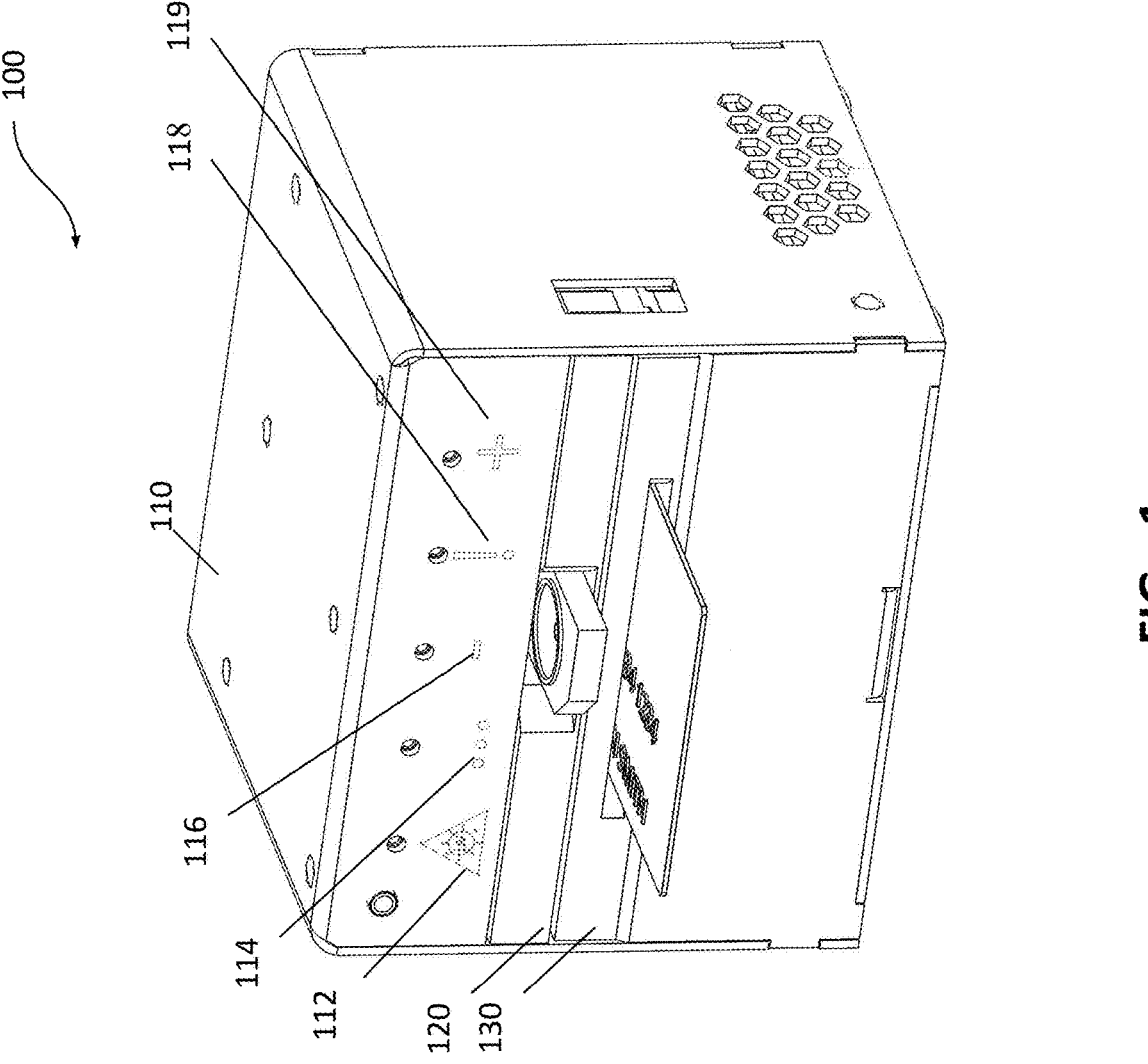
FIG. 1 depicts an orthogonal view of a testing device according to an embodiment of the present invention.

The diagrams depicted herein are illustrative. There can be many variations to the diagrams or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two- or three-digit reference numbers. With minor exceptions, the leftmost digit(s) of each reference number corresponds to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of +8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, present testing systems receive a range of cassettes and samples to be tested. These samples will often carry bacteria and viruses that may then be spread. Given the prominence of deadly pathogens in today's environment, it is imperative to cleanse these testing systems. Unfortunately, present testing systems often lack a cleaning or sterilization feature or cycle. Thus, harmful bacteria and viruses can spread. Additionally, future test samples may be contaminated by past test samples rendering test results invalid with the possibility for false positives.

Turning now to an overview of the aspects of the invention, embodiments of the present invention provide a UVC light source to sterilize test surfaces and surrounding. The UVC light source is triggered by an imaging device capturing an image of a visual feature that activates the UVC light source. This visual feature may be ever present in the viewing field of the imaging device, and thus frequently activated whenever a sample carrier is removed from the imaging device's field of view or may be activated by insertion of a carrier with a visual feature that triggers that sanitization cycle, i.e., activation of UVC lights, for example, for a period of time. In order to protect the imaging source, a UVC filter may be placed in front of the imaging device.

While the discussion in this description uses testing for SARS-COV-2 to discuss embodiments of the invention, those skilled in the art after reading this specification will appreciate that similar techniques can be used to standardize testing of multiple viruses or substances to standardize test results. These test results are standardized across testing techniques and across testing products and protocols of a range of test manufacturers. Regardless of test kit maker, health care professionals can be provided with a standardized result that has meaning beyond positive and negative results.

As previously mentioned, embodiments of the present invention can be implemented with a testing device that provides fast results. RAPID™ (which is an acronym for Reliable Accurate Practical Inexpensive Diagnostics) antigen and antibody tests and associated reading methods become crucial in improving the speed and quality of test data. Because the invention described herein uses a computerized reader rather than relying on human interpretation, systems and method described herein are not only more accurate in differentiating a positive from a negative from an invalid test result, but they may also visually read and store the actual concentration of the pathogen so that analytics can be performed across a large number of patients, which can in turn be used by government, research institutes, vaccine developers, and pandemic planners implementing prevention measures to reduce the spread of future diseases. This concentration, which is based on intensity of the test line, is also used to determine an eCt that can be used by health professionals to guide treatment.

In addition, the testing device of the present invention includes a powerful computer that can store testing protocols for a full gauntlet of different tests as well as equivalence curves that are used to convert intensity of a read test line to an eCt or other appropriate standardized, equivalent results. Tests are not limited to COVID-19 testing, but can include reading any type of test strip, or test carriage, for any type of disease, syndrome, virus, or bacteria. The results of any of these tests are uploaded to a central database for providing to the patient and for later use and analysis. Data collected in the central database may be anonymized for data mining purposes.

The testing device may also communicate with a web browser or dedicated app on a patient's mobile phone, tablet, or computer for providing the patient with test results and logging.

FIG. 1 depicts an orthogonal view of a testing device 100 according to an embodiment of the present invention. The testing device 100 is enclosed by a case 110. The case 110 includes a plurality of electronics for analyzing a lateral flow assay ("LFA") strip present in an assay tube or cassette. References to LFA throughout this specification include references to lateral flow tests, rapid antigen tests, and antigen card tests. A removable carrier 120 has an opening in which the assay tube, cassette, or card is placed. During the remainder of this description, whenever the term "cassette" is used that term includes any of an assay tube, cassette, or card. The LFA strip provides indicators (stripes at various places along the LFA strip) that indicate the presence of analytes present in a sample. The testing device 100 includes an LFA strip reader having a plurality of LED's at a variety of wavelengths that shine upon the sample and a camera that images the sample, sending the image to a computer present in the testing device 100 for analysis. As a relatively powerful computer receives the image of the LFA strip, the computer can adjust for any misalignment of samples or changes to characteristics of the paper that the LFA strip is made from. In addition, in exemplary embodiments of the invention, one of the light sources can provide UVC light for sterilizing the testing device 100 prior to a new assay tube or cassette being placed in the testing device 100.

The camera in the device not only reads the LFA strip, but also any barcode, providing both images to the computer in the testing device 100. When a barcode is not present, the camera provides a visual feature to the computer. Such a visual feature may be the shape of the inserted cassette, text on the cassette, presence or absence of one or more barcodes, data matrices or QR codes, or one or more colors present on the cassette, for example. The computer may then associate the unique ID with the test results and upload the results to a central database where it is provided back to the patient and/or caregiver.

As the testing device 100 may be a headless device (one lacking a keyboard or screen for input and a screen or printer for output), a plurality of indicators on an indication panel is present on the front of the testing device 100 for indicating, for example, disinfecting in process 112, testing-in-process 114, negative results 116, invalid 118, or positive results 119 from the sample.

Testing device 100 also includes a patient identification reader for reading patient identification information, such as card reader 130 for reading an identification card from a patient to associate the patient with the received assay tube or cassette. In an exemplary embodiment of the invention, the card reader may be a smart card reader to read a government issued ID, such as a passport, national ID card, health card, or smart driver's license or it may read a credit card associated with the patient. Those skilled in the art will appreciate after reading this disclosure that other readers may also be used: for example, near field communication from a patient's device, such as her mobile phone, may be used to associate the patient with the sample or a magnetic strip may be read from a credit card lacking a smart chip.

These variations are all contemplated to be used. In this way, when using the testing device 100 with cassettes that lack a unique identifier, the test result remains associated with the patient. No user input is needed beyond the identification card.

As stated previously, the testing device 100 may be in communication over, for example, Ethernet, WiFi, or mobile communications (such as 3G, 4G, and 5G, for example, to a central database. Test results, including standardized results, such as eCt, are linked to the patient at the testing device 100 and provided to the central database following a test. The test results may then be further shared with the patient's healthcare provider and/or directly to the patient. A rich database of information is developed in the central patient database, and following anonymization, may be mined for demographic or other information relating to the test being taken.

Linking the testing device 100 to a central server also provides an additional benefit, as new tests are developed that use LFA strips, new profiles for tests may be downloaded, either automatically or pushed manually, from a central test database to the testing device 100. Thus, there is no need for expensive field technicians to update the testing device 100. Such updates happen automatically. These profiles include not only testing information, but also equivalence curves used by testing device 100 to convert intensity measurements of the test line to an equivalent, standardized result.

Figure 2:
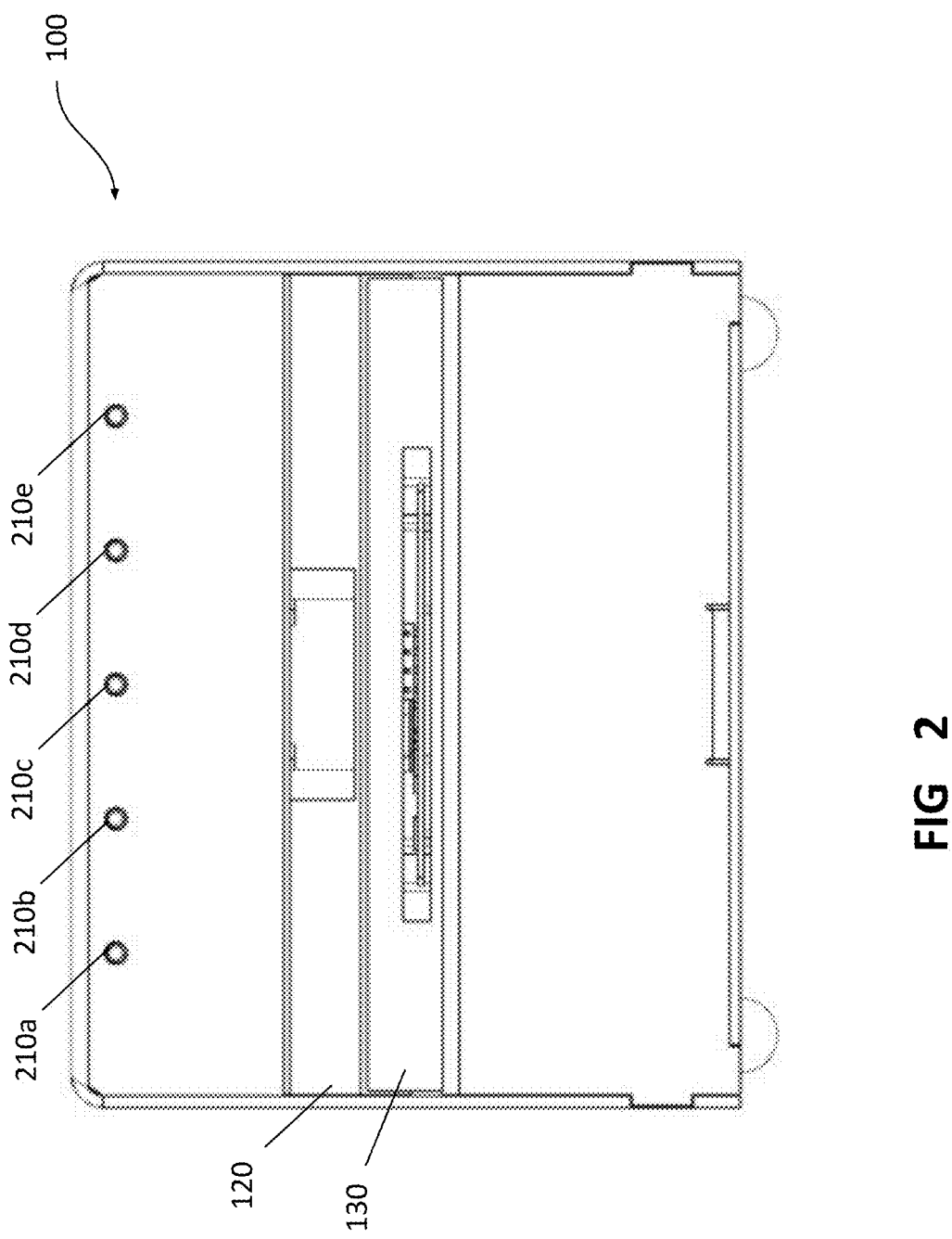
FIG. 2 depicts a front view of the testing device according to an embodiment of the present invention.

FIG. 2 depicts a front view of the testing device 100 according to an embodiment of the present invention. The front view again shows the removable carrier 120 for holding a cassette or assay tube and the card reader 130. In addition, five indicators, for example LED's, provide test results to a patient who is using the test device 100. In an exemplary embodiment, a sterilization indicator 210a that shows when sterilization activity is occurring within testing device 100, connectivity indicator 210b, positive result indicator 210c, fault indicator 210d, and negative result indicator 210e may be provided. An additional power indicator with a power button 440 may be included to power the testing device 100 on and off.

Figure 3:
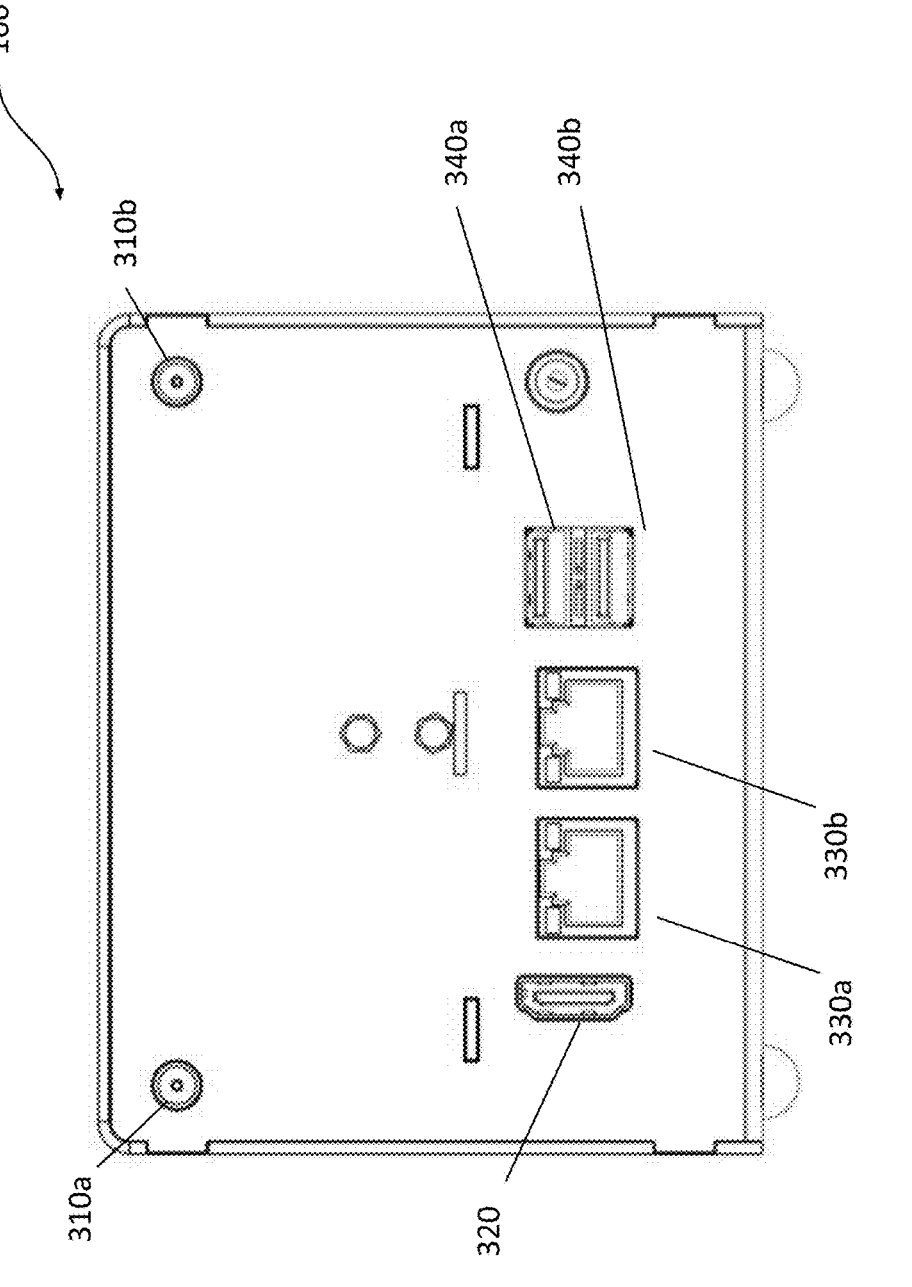
FIG. 3 depicts a back view of the testing device according to an embodiment of the present invention.

FIG. 3 depicts a back view of the testing device 100 according to an embodiment of the present invention. The back view of the testing device 100 shows various connectivity features present in an exemplary testing device 100. Testing device 100 may have a port for a display, such as HDMI port 320, Ethernet ports 330a and 330b, and USB ports 340a and 340b, and other connectors 310a, 310b. Thus, while the testing device is primarily designed to be headless, if placed in a lab or a doctor's office the testing device also supports connection to a monitor and a keyboard. Results may then be shared with a healthcare professional on the display, and since the testing device 100 includes a full computer, it can support additional functions for the healthcare provider. Additionally, a sterilization interrupt button may be provided in communication with the processor of the testing device in order to trigger a sterilization process interrupt request.

Figure 4A:
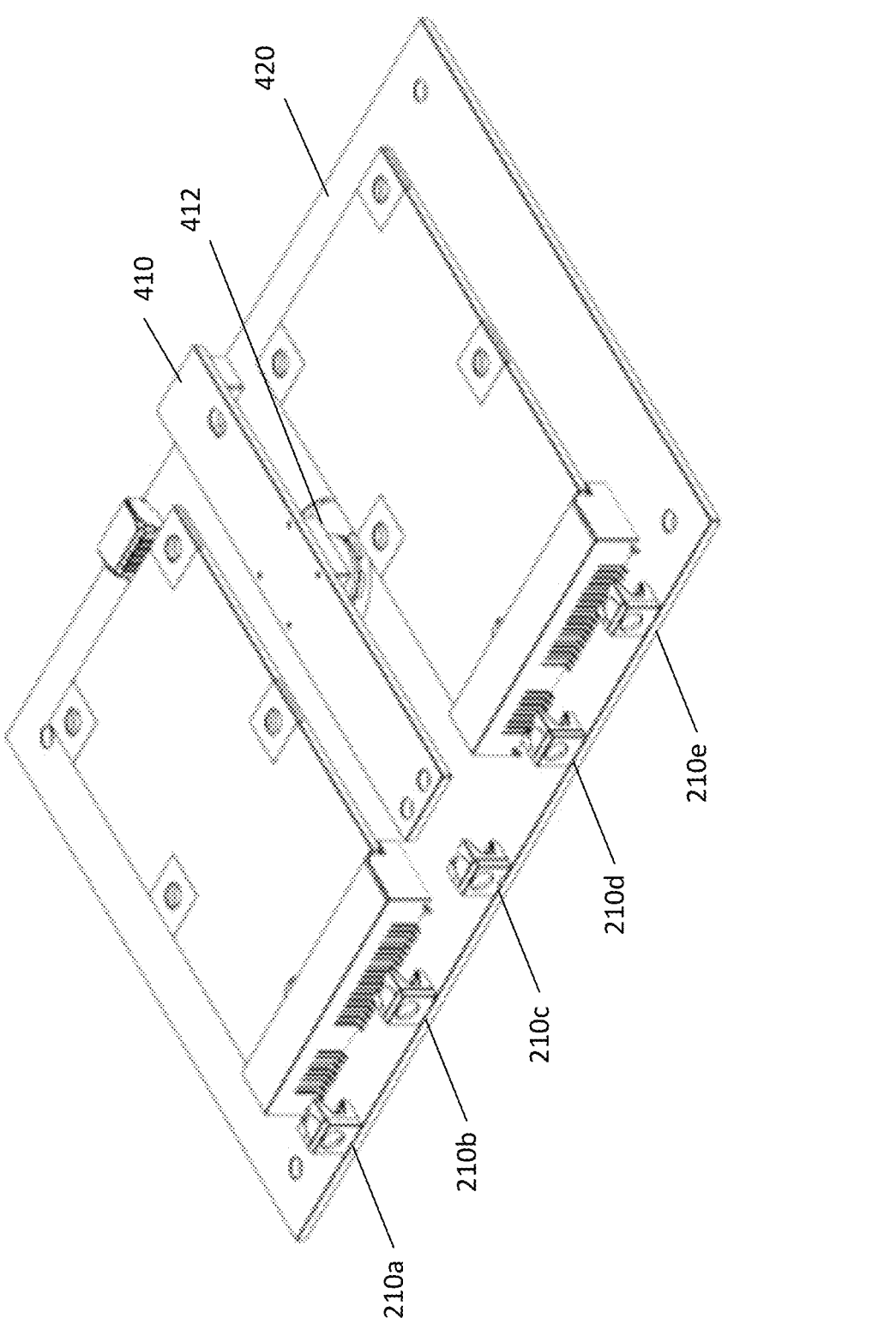
FIG. 4a depicts an orthogonal view of an LED testing and indicating board within the testing device according to an embodiment of the present invention.

FIG. 4a depicts an orthogonal view of an LED testing 410 board and indicating board 420 within the testing device 100 according to an embodiment of the present invention. The LED testing board 410 includes a plurality of LED's (not shown) to provide a variety of wavelengths of light that shine upon the LFA strip. The LED testing board 410 may include one or more UVC light sources (not shown) to sterilize the portion of the testing device 100 that comes in contact with the sample. The LED testing board 410 includes a camera to take an image of a barcode present on an assay tube and of any LFA strips inserted into the testing device 100. These images are then communicated to the on-board computer within the testing device 100. The LED testing board 410 resides on the indicating board 420 that supports the indicators previously described. A hole in the indicating board 420 allows for a camera 412 on the LED testing board 410 to view the LFA strip. Camera 412 may be protected from damage that may be caused by UVC light sources by having a UV filter (not shown) placed in front of a lens of camera 412. The LED testing board also contains a temperature and a humidity sensor.

Figure 4B:
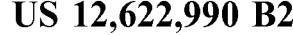
FIG. 4b depicts an orthogonal view of another embodiment of an indicating board within the testing device according to an embodiment of the present invention.

FIG. 4b depicts an orthogonal view of another exemplary embodiment of the indicating board 420 within the testing device 100 according to an embodiment of the present invention. A power switch 440 may be provided on the indicating board 420 to power the testing device 100 on and off. A multi-port USB connector 430 may be provided that allows a carrier, such as sample carrier 120 to have electronic features that communicate with a host PC and its software. The positioning of the USB connectors relative to the sample carriers are aligned such that a PCB mounted within the sample carrier can use edge gold fingers in the same position as a typical USB connector, thus eliminating the need for an actual USB connector to be mounted on the PCB, and the USB connection between the PCB and the USB connector 430 is made when the sample carrier is inserted.

Figure 5A:
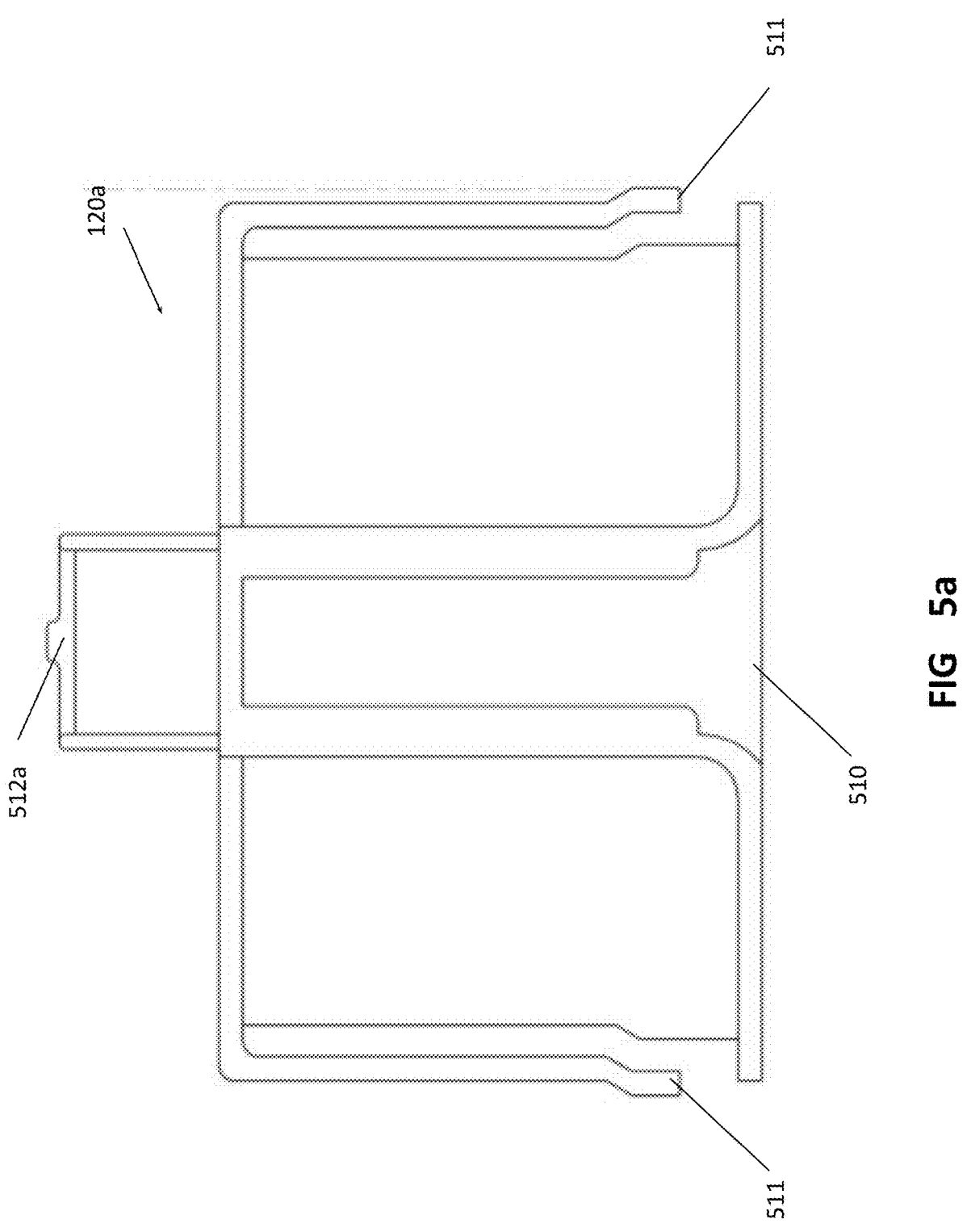
FIG. 5a depicts a top-down view of a first sample carrier used in the testing device according to an embodiment of the present invention.

FIG. 5a depicts a top-down view of a first sample carrier 120a used in the testing device according to an embodiment of the present invention. The sample carrier 120a receives an assay tube or carriage containing an LFA strip in opening 510 and supports it while camera 412 takes an image of the LFA strip. It is removable in an exemplary embodiment, so that as testing carriages or assay tubes change in the future, it may be swapped out. The sample carrier may include an active USB controller coupled to a mechanical switch or photo-optical device for sensing the presence of the assay tube or carriage. There are features on the sides 511 to latch with the chassis as the sample carrier is installed in the chassis, and a structure that serves like a spring 512a in the rear both holding the carrier in place during shipping and providing tension.

Figure 5B:
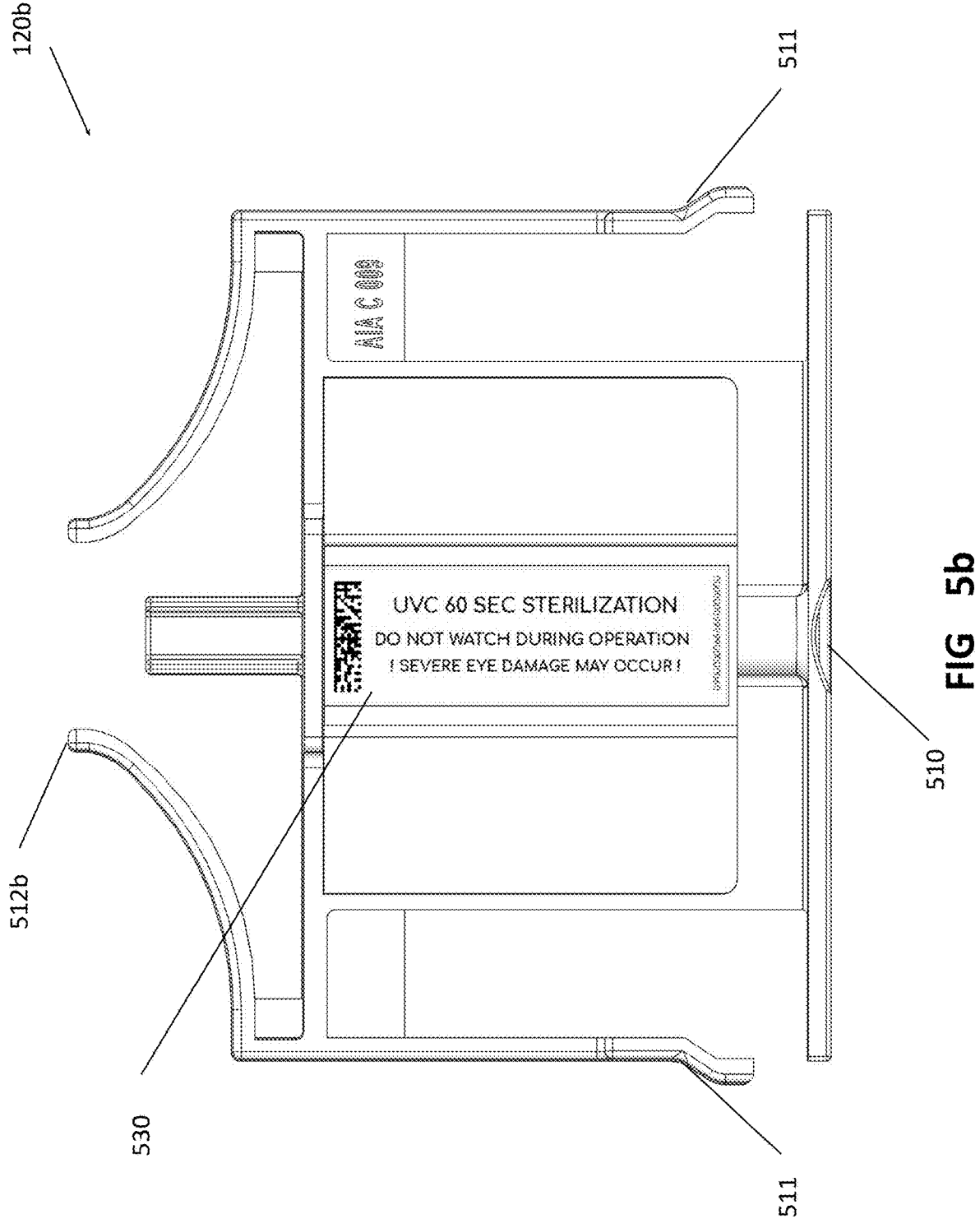
FIG. 5b depicts a top-down view of a second sample carrier used in the testing device according to an embodiment of the present invention.

FIG. 5b depicts a top-down view of a second sample carrier 120b used in the testing device according to an embodiment of the present invention. The sample carrier 120b receives an assay tube or carriage containing an LFA strip in opening 510 and supports it while camera 412 takes an image of the LFA strip. It is removable in an exemplary embodiment, so that as testing carriages or assay tubes change in the future, it may be swapped out. The sample carrier may include an active USB controller coupled to a mechanical switch or photo-optical device for sensing the presence of the assay tube or carriage. There are features on the sides 511 to latch with the chassis as the sample carrier is installed in the chassis, and a structure that serves like a spring 512b in the rear both holding the carrier in place during shipping and providing tension. Furthermore, a label 530 containing a sterilization code, such as a barcode or QR code, may be placed on either second sample carrier 120b or first sample carrier 120a which may trigger a sterilization function, such as activation of the UVC light sources, when read by camera 412.

Figure 5C:
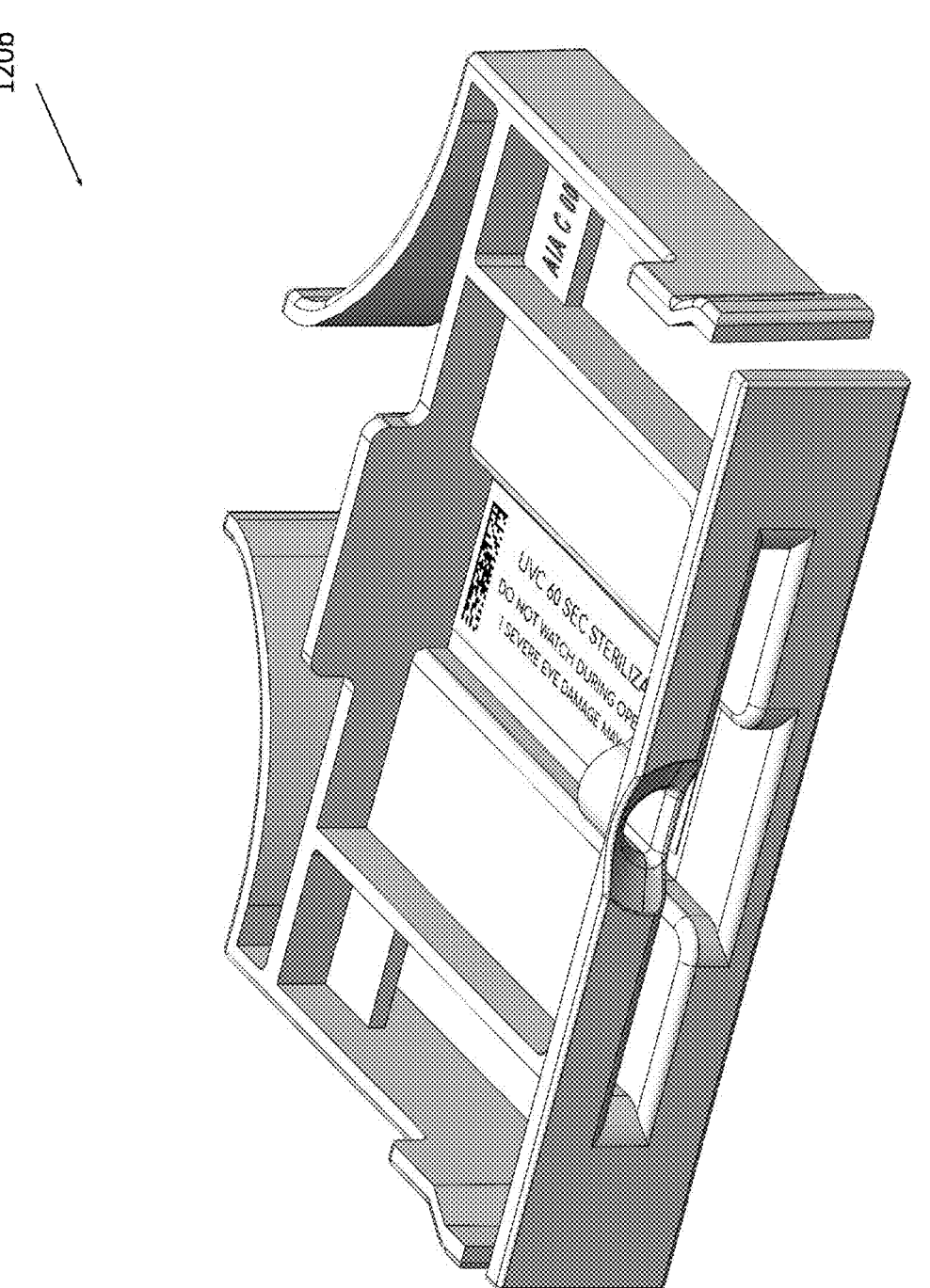
FIG. 5c depicts an orthogonal view of the second sample carrier used in the testing device which has a sterilization barcode sticker internal to the second sample carrier according to an embodiment of the present invention.
Figure 5D:
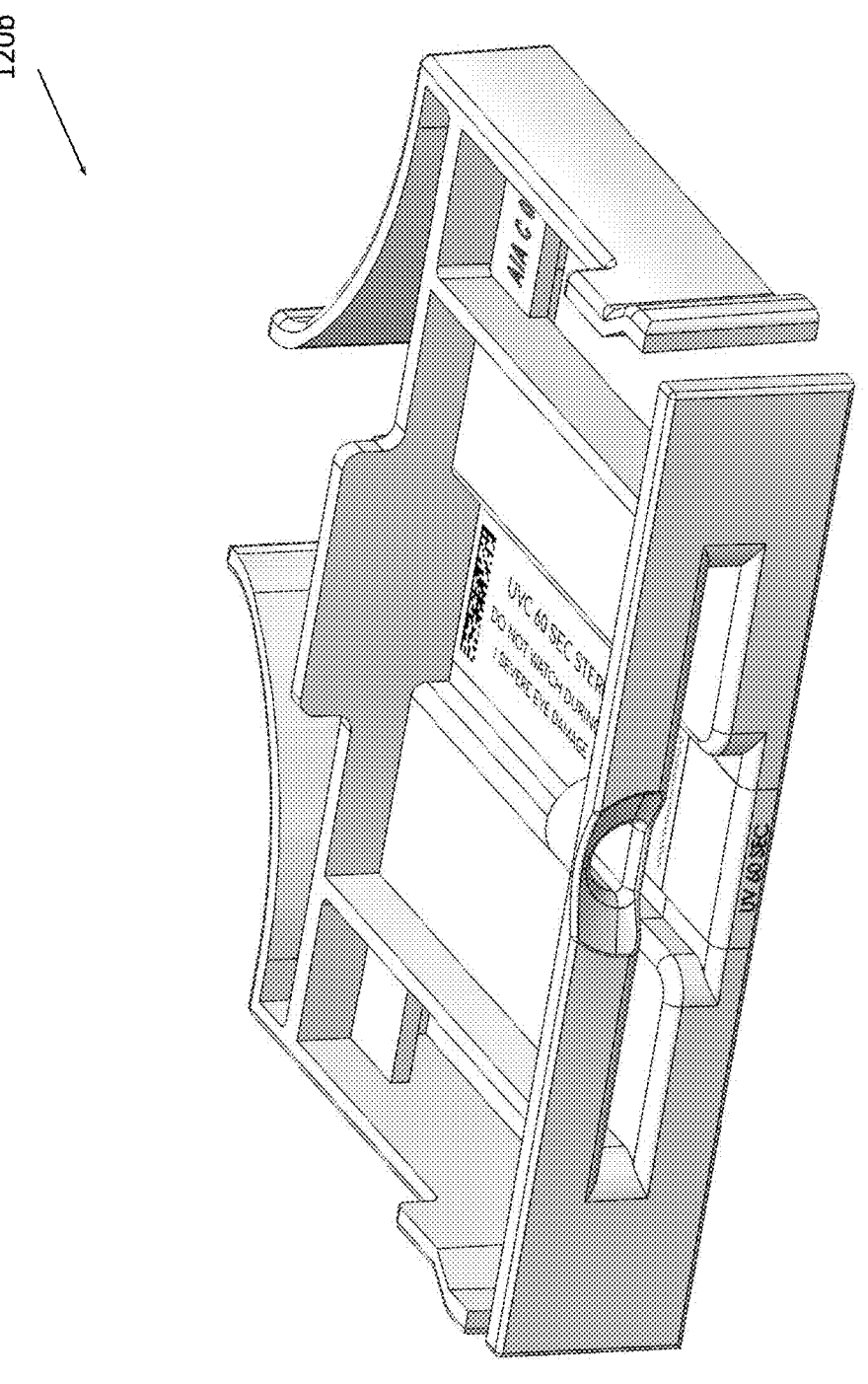
FIG. 5d depicts an orthogonal view of the second sample carrier used in the testing device which has a sterilization barcode sticker which is both internal and external to the second sample carrier according to an embodiment of the present invention.

FIG. 5c depicts an orthogonal view of the second sample carrier 120b used in the testing device which has a sterilization barcode sticker internal to the second sample carrier according to an embodiment of the present invention. FIG.

5d depicts an orthogonal view of the second sample carrier 120b used in the testing device which has a sterilization barcode sticker which is both internal and external to the second sample carrier according to an embodiment of the present invention.

Figure 6A:
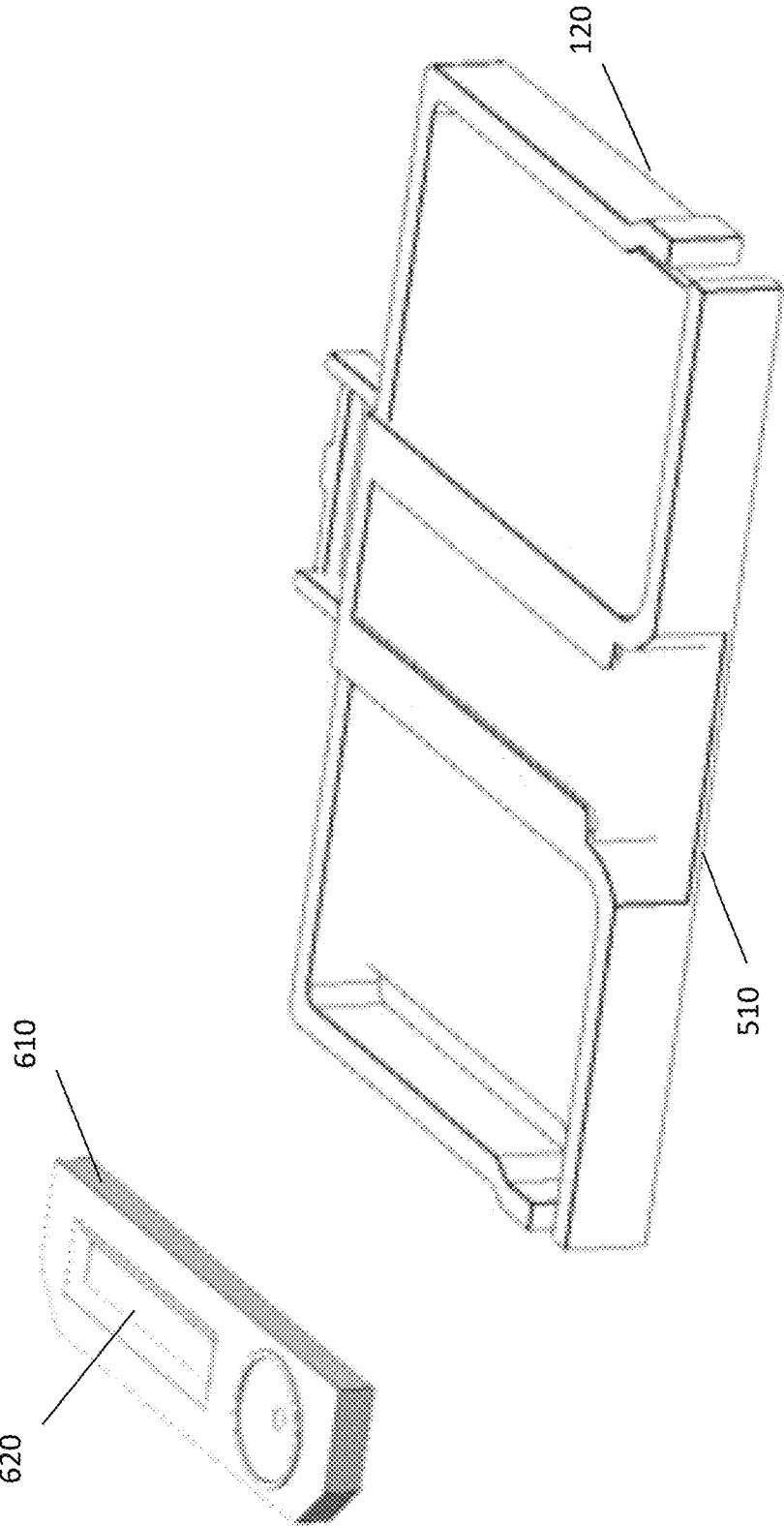
FIG. 6a depicts an orthogonal view of the sample carrier with a sample cassette used in the testing device according to an embodiment of the present invention.
Figure 6B:
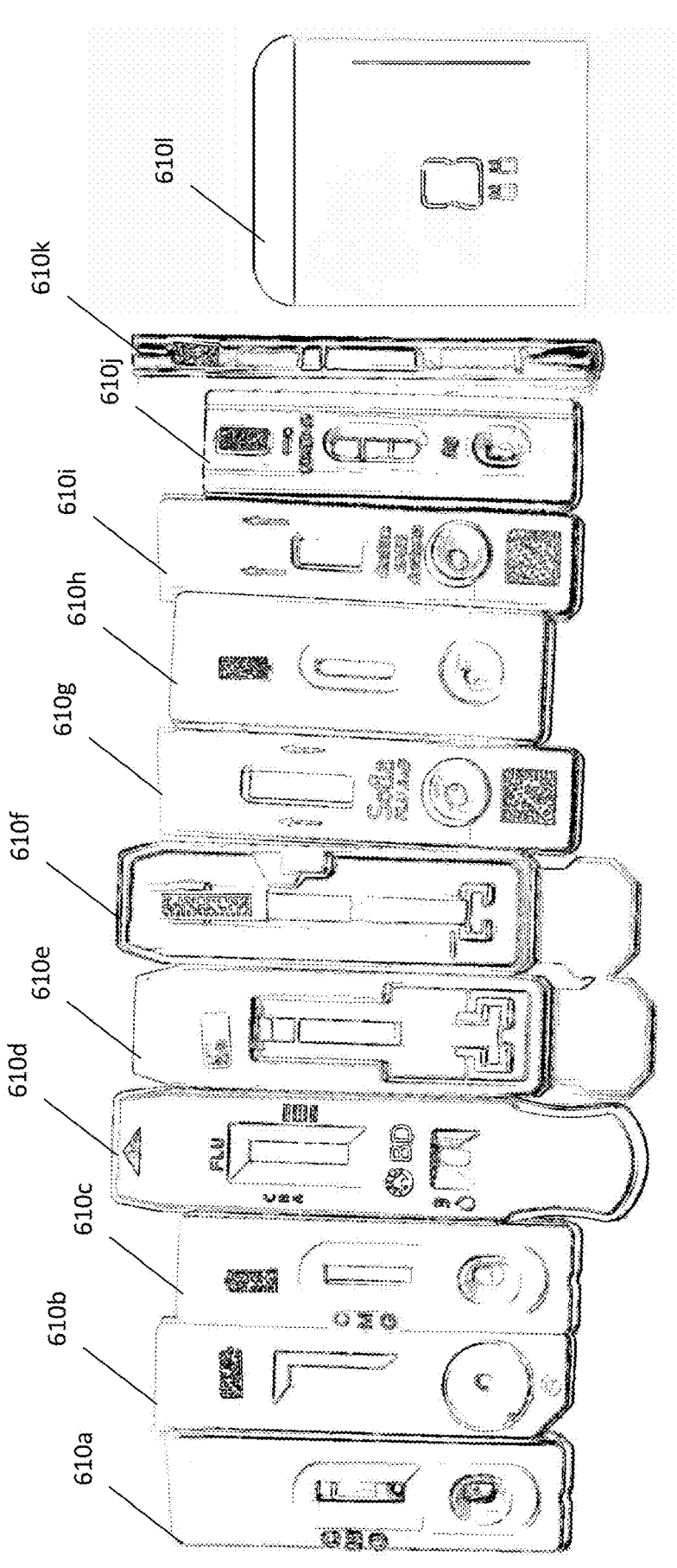
FIG. 6b depicts a plurality of cassettes that may be used in conjunction with the testing device according to an embodiment of the present invention.

FIG. 6a depicts an orthogonal view of the sample carrier 120a with a sample cassette 610 containing an LFA strip 620 used in the testing device 100 according to an embodiment of the present invention. FIG. 6b depicts a plurality of cassettes 610a-l that may be used in conjunction with the testing device 100. Cassette 610k is a clear assay and cassette 610l is a card containing an LFA test strip.

Figure 6C:
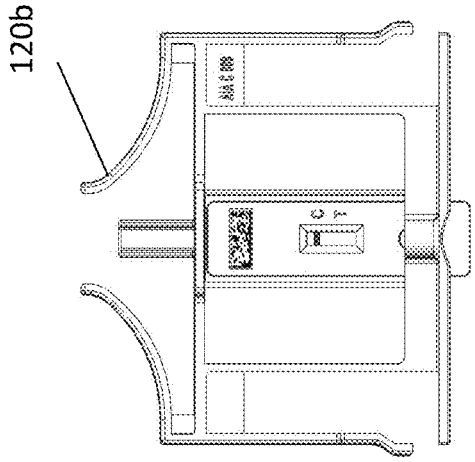
FIG. 6c depicts the cassette containing the lateral flow assay strip being inserted into the second carrier which contains a sterilization barcode sticker according to an embodiment of the present invention.
Figure 6C:
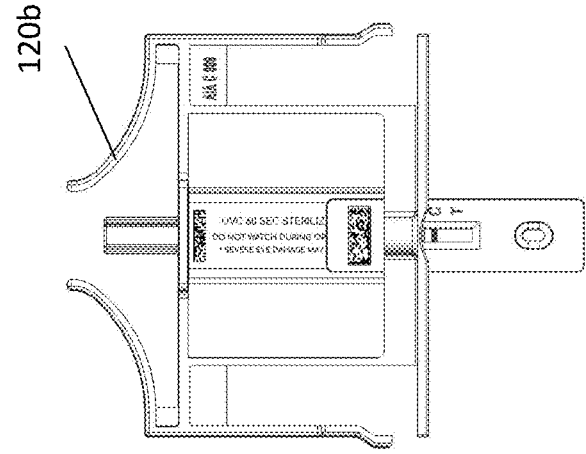
Figure 6C:
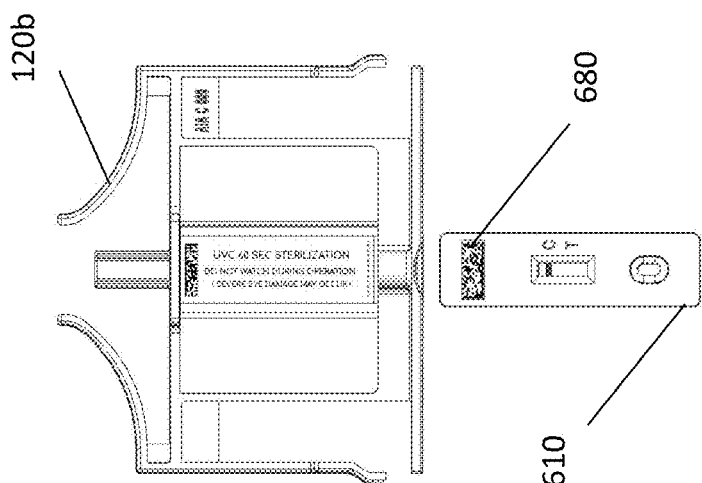

FIG. 6c depicts the cassette 610 containing the lateral flow assay strip 620 being inserted into the second carrier 120b which contains a sterilization barcode sticker according to an embodiment of the present invention. As the cassette 610 is inserted over time, as shown in this figure, a code 680 that identifies the cassette replaces the label 530 in the field of vision of camera 412, so that the testing device 100 will initiate a scan of the lateral flow assay strip to provide a test result.

Figure 6D:
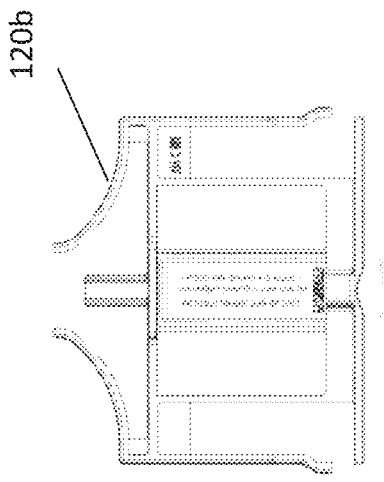
FIG. 6d depicts a sterilization cassette having a sterilization code being inserted into the second carrier where the second carrier lacks a sterilization barcode sticker according to an embodiment of the present invention.
Figure 6D:
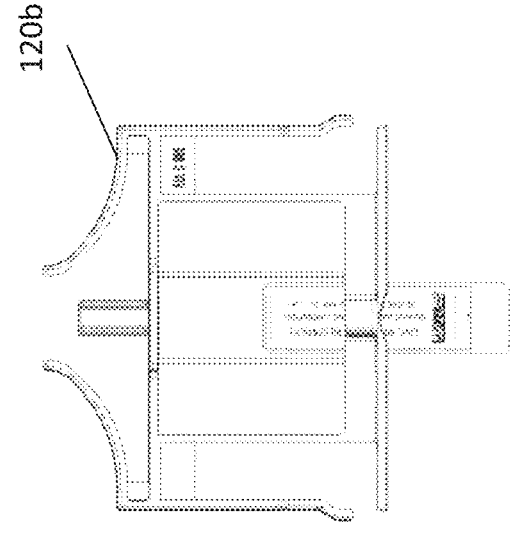
Figure 6D:
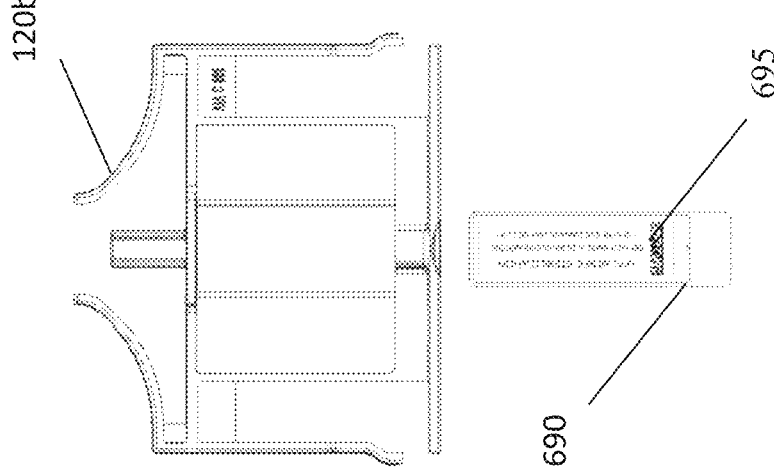

FIG. 6d depicts a sterilization cassette 690 having a sterilization code 695 being inserted into the second carrier 120b where the second carrier 120b lacks a sterilization barcode sticker according to an embodiment of the present invention. Inserting the sterilization cassette 690 triggers a sterilization process, i.e., activation of the UVC light source, when the sterilization code is read by camera 412.

Figure 6E:
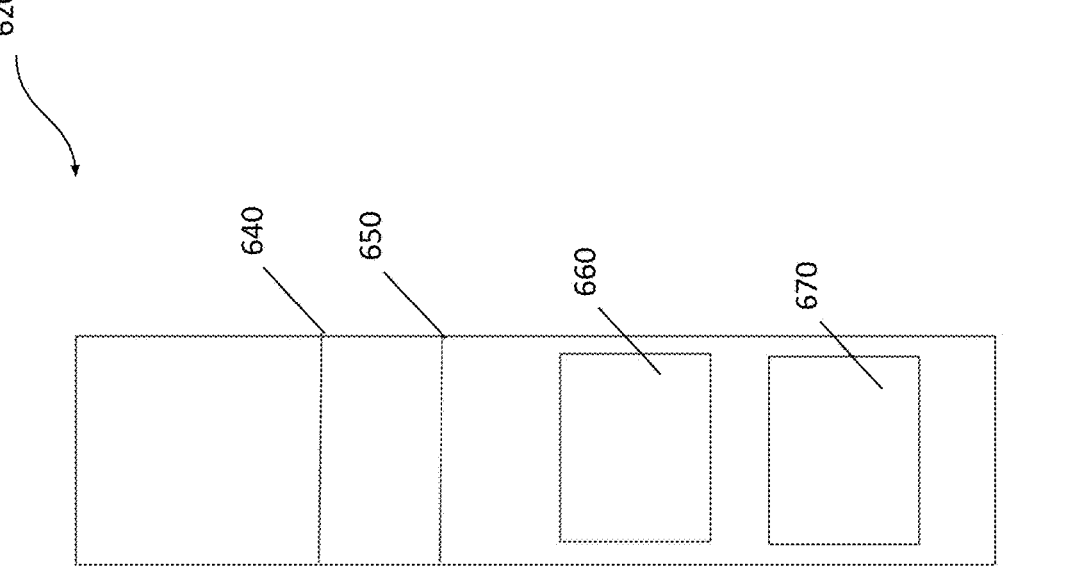
FIG. 6e depicts the LFA strip 620 within the cassette 610 according to an embodiment of the present invention.

FIG. 6e depicts the LFA strip 620 within the cassette 610 according to an embodiment of the present invention. The LFA strip 620 has at least one control line 640, test line 650, conjugate pad 660, and analyte pad 670. An analyte containing a sample from a domain is placed on the analyte pad 670. The analyte flows up the LFA strip 620 through the area of the strip having the conjugate pad 660, test line 650, and control line 640. Testing systems may be used in multiple domains. The domain, mentioned above, is the human domain, but testing is also performed in other domains, such as animals and the environment, for example. Reference to a domain herein is reference to any situation, for example, human testing, animal testing, environmental testing, and food testing.

The material of the test line 650 provides a positive result in the presence of a chemical-of-interest being tested for in the domain and a negative result in the absence of the chemical-of-interest being tested for in the domain. Where the chemical-of-interest can be a pathogen, or a piece of a pathogen, a biological marker, such as a protein of a chemical organic or inorganic, and where the biological marker can specifically be a substance such as the active ingredient in a drug, food additive, or environmental pollutant. The intensity of the test line 650 is measured by testing device 100, either visually or through the conductivity probes described earlier, in order to be used with the equivalence curve to determine an equivalent, standardized result, such as an eCt value.

Figure 7A:
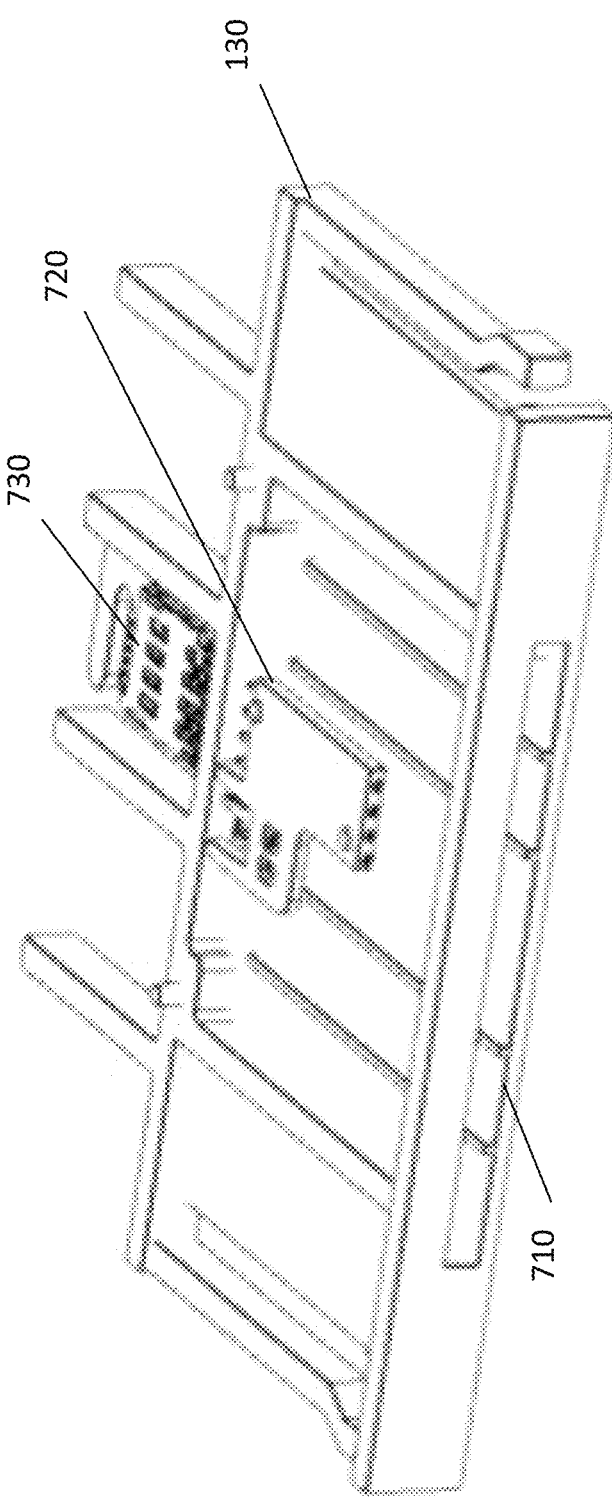
FIG. 7a depicts an orthogonal view of a card reader used in the testing device according to an embodiment of the present invention.

FIG. 7a depicts an orthogonal view of a removable card reader 130 used in the testing device 100 according to an embodiment of the present invention. As previously discussed, the card reader 130 receives a smart card, such as a credit card or national ID card, via slot 710, reads it with smart reader 720, and provides the read information to the computer within the testing device 100. In alternative embodiments, the removable card reader 130 can read magnetic strips on credit cards or be modified for near field communication to read identifying information from a patient's mobile phone or tablet. In another alternative embodiment, an external reader may be used to read optical or near field communication information from patient identification, such as a passport. Identity collection accessories include the removable card reader 130 and the external reader.

Removable card reader 130 may have a secondary smart card reader 740 for inserting a smart card from a health care provider, such as a medical professional. For example in Taiwan doctors' offices have smart card readers where patients can insert their cards, but the reader also requires a second smart card to be inserted by the doctor with their credentials for added security. The health care provider's smart card would be inserted into a second card or smart card slot 730 before the removable card reader 130 is inserted into the testing device 100.

Figure 7B:
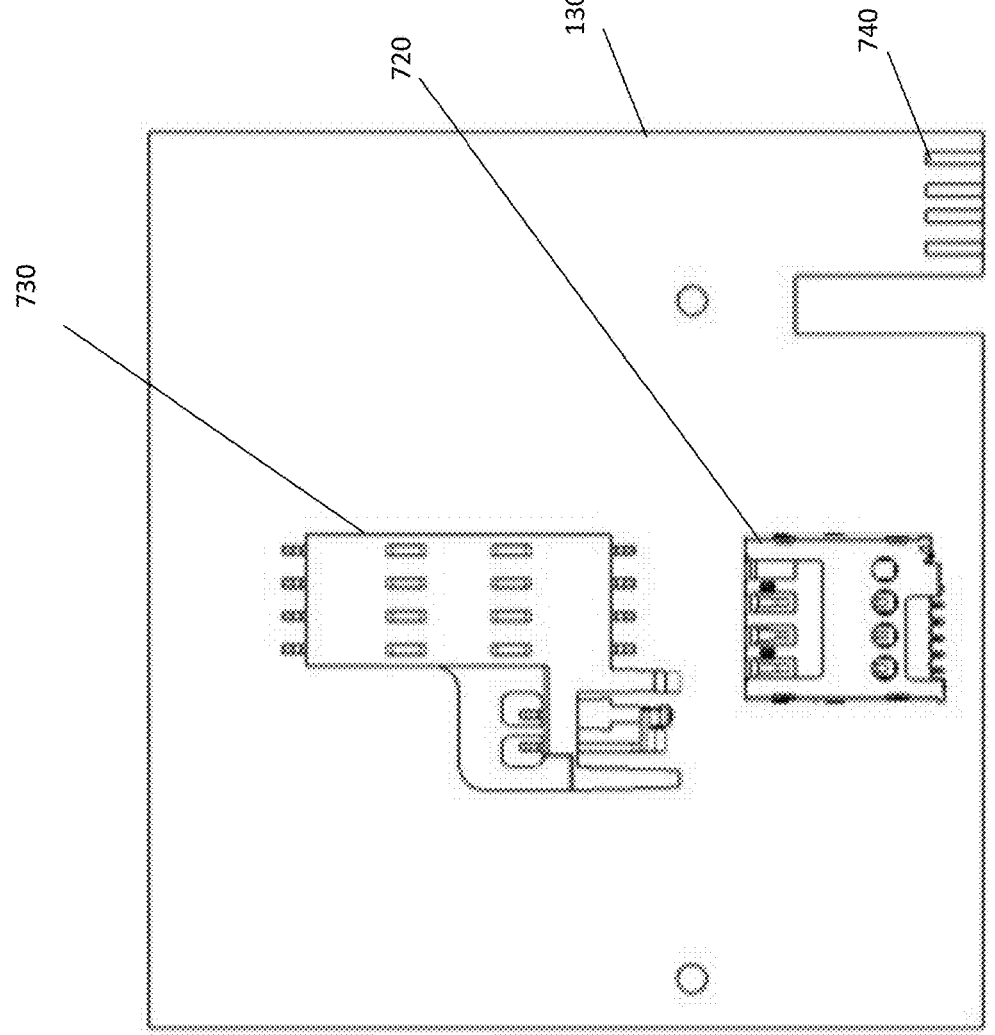
FIG. 7b depicts a top view of the card reader used in the testing device according to an embodiment of the present invention.

The removable card reader 130 may have gold fingers to permit the removable card reader 130 to be plugged into the USB connector 340, without having to physically mate a printed circuit board in the removable card reader 130 with a computer 800 (discussed with respect to FIG. 8 below). The removable card reader 130 may also be configured to receive the smart card upside down. This configuration would place the smart card reader 740 facing up on a floor of the removable card reader 130 and include a camera above the removable card reader 130 to read and communicate a signature from the smart card to the computer 800. FIG. 7b depicts a top view of the card reader used in the testing device according to an embodiment of the present invention.

In an alternative embodiment of the invention, instead of a card reader being separated from the sample carrier, the card reader and sample carrier are in the same reception tray, such that an identification card (such as a driver's license) and assay tube or carriage are inserted side-by-side. In this embodiment, two cameras above the reception tray may be used, where a first camera reads the assay tube or carriage and a second camera reads the identification card visually, such as by PDF-417. PDF417 is a stacked linear barcode format used in a variety of applications such as transport, identification cards, and inventory management. "PDF" stands for Portable Data File. The "417" signifies that each pattern in the code consists of 4 bars and spaces in a pattern that is 17 units (modules) long.

Figure 8:
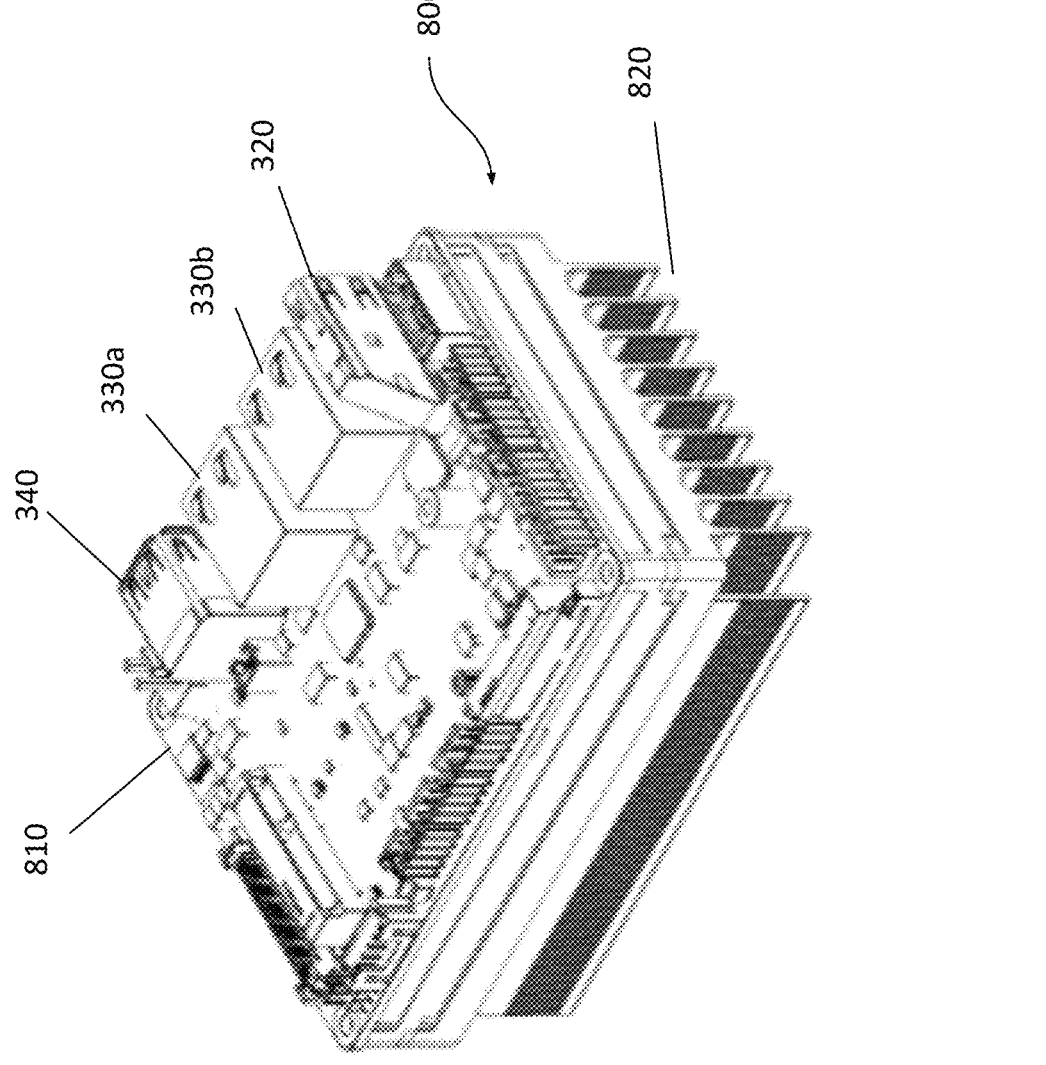
FIG. 8 depicts an orthogonal view of a computer used in the testing device according to an embodiment of the present invention.

FIG. 8 depicts an orthogonal view of a computer 800 used in the testing device 100 according to an embodiment of the present invention. The computer 800 will be described in more detail in FIG. 9, but includes a PC board or Motherboard 810, along with a heat sink 820. In an exemplary embodiment, the computer 800 resides in the bottom of the testing device 100 and is physically separated from the sample carrier 120. The computer hosts the ports 320, 330, and 340 previously discussed.

Figure 9:
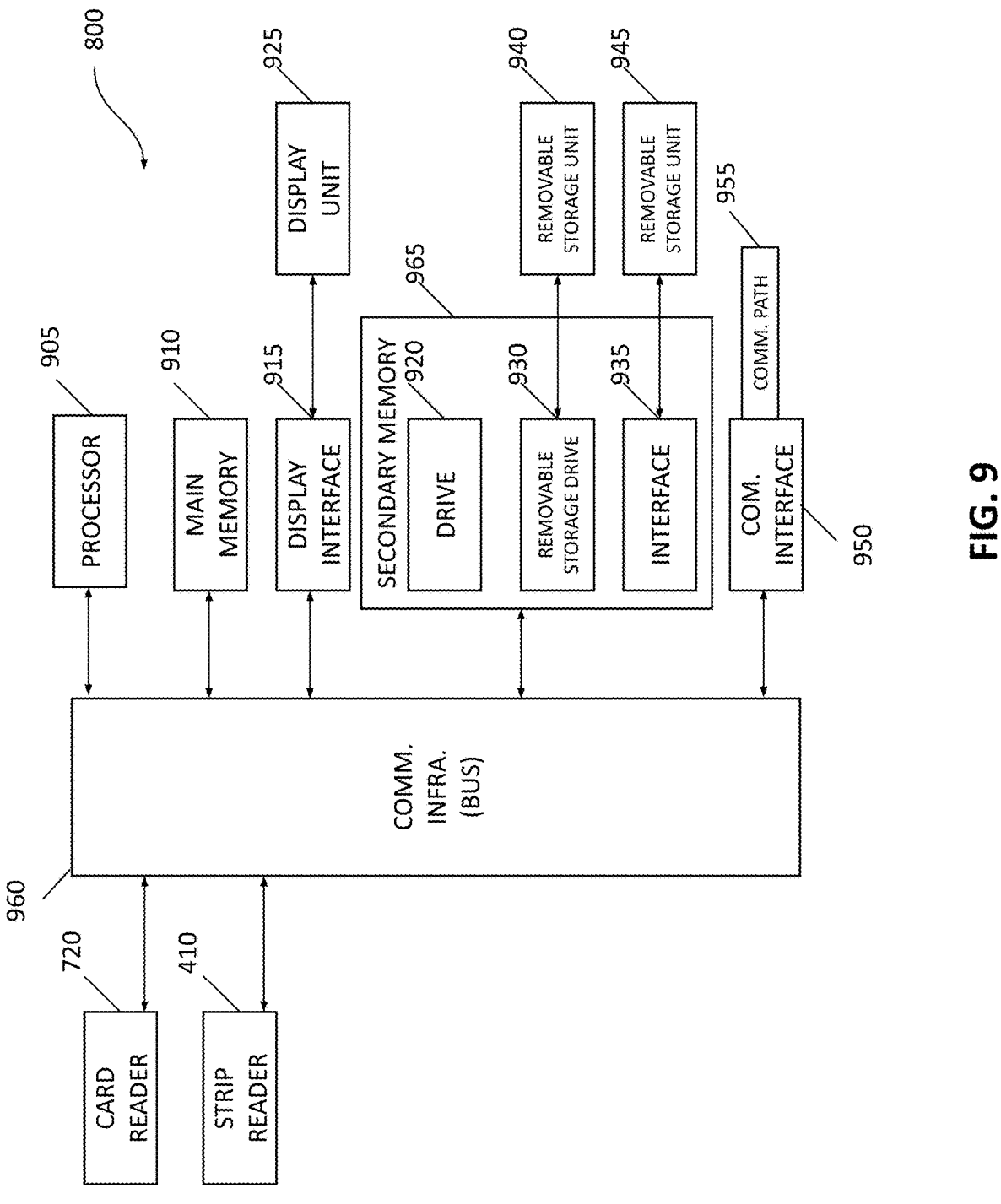
FIG. 9 depicts a block diagram of the computer used in the testing device according to an embodiment of the present invention.

FIG. 9 depicts a block diagram of the computer 800 used in the testing device according to an embodiment of the present invention. FIG. 9 depicts a high-level block diagram computer system 800, which can be used to implement one or more aspects of the present invention. More specifically, computer system 800 can be used to implement some hardware components of embodiments of the present invention. Although one exemplary computer system 800 is shown, those skilled in the art after reading this disclosure will understand that other implementations are also possible. Computer system 800 includes a communication path 955, which connects computer system 800 to additional systems (not depicted) and can include one or more wide area networks (WANs) and/or local area networks (LANs) such as the Internet, intranet(s), and/or wireless communication network(s). In one exemplary embodiment, communication path 955 includes wireless local area network communication, mobile or cellular wireless communication, and wired (such as Ethernet) communication. Computer system 800 is in communication via communication path 955, e.g., to communicate data between them. The computer system 800 may also contain an optional internal battery and battery charger that allows the unit to be charged. Alternatively, an external battery with a power cord connected to the unit may be used, where the external battery unit features the same input connector as the computer system, and the external battery unit may then be installed in the field to provide robustness against power outages or to be used in the field where wall power is not available. An example of such as device is sown in FIG. 15

Computer system 800 includes one or more processors, such as processor 905. Processor 905 is connected to a communication infrastructure 960 (e.g., a communications bus, cross-over bar, or network). Computer system 900 can include a display interface 915 that forwards graphics, text, and other data from communication infrastructure 960 (or from a frame buffer not shown) for display on a display unit 925. In a headless device, such as testing device 100, no display unit is present 925, although one may be added by connecting to HDMI port 320. Computer system 900 also includes a main memory 910, preferably random access memory (RAM), and can also include a secondary memory 965. Secondary memory 965 can include, for example, a hard disk or solid-state drive 920 and/or a removable storage drive 930, representing, for example, a floppy disk drive, a magnetic tape drive, or an optical disk drive. Removable storage drive 930 reads from and/or writes to a removable storage unit 940 in a manner well known to those having ordinary skill in the art. Removable storage unit 940 represents, for example, a floppy disk, a compact disc, a magnetic tape, solid state, or an optical disk, etc. which is read by and written to by removable storage drive 930. As will be appreciated, removable storage unit 940 includes a computer readable medium having stored therein computer software and/or data.

In alternative embodiments, secondary memory 965 can include other similar means for allowing computer programs or other instructions to be loaded into the computer system. Such means can include, for example, a removable storage unit 945 and an interface 935. Examples of such means can include a program package and package interface (such as that found in video game devices), a removable memory chip (such as an EPROM, or PROM) and associated socket, and other removable storage units 945 and interfaces 935 which allow software and data to be transferred from the removable storage unit 945 to computer system 800.

Computer system 800 can also include a communications interface 950. Communications interface 950 allows software and data to be transferred between the computer system and external devices. Examples of communications interface 950 can include a mobile modem using, for example, 3G, 4G/LTE, 5G, and future mobile standard networks, a network interface (such as an Ethernet card), a communications port, or a PCI, Mini PCI, or PCIe slot and card, for example. Software and data transferred via communications interface 950 are in the form of signals which can be, for example, electronic, electromagnetic, optical, or other signals capable of being received by communications interface 950. These signals are provided to communications interface 950 via communication path (i.e., channel) 935. Communication path 935 carries signals and can be implemented using wire or cable, fiber optics, a phone line, a cellular or mobile phone link, an RF link, and/or other communications channels.

In the present description, the terms "computer program medium," "computer usable medium," and "computer readable medium" are used to generally refer to media such as main memory 910 and secondary memory 965, removable storage drive 930, and a hard disk installed in hard disk drive 920. It may also refer to flash storage options, such as USB thumb drives or SD cards. Computer programs (also called computer control logic) are stored in main memory 910 and/or secondary memory 965. Computer programs can also be received via communications interface 390. Such computer programs, when run, enable the computer system to perform the features of the present invention as discussed herein. In particular, the computer programs, when run, enable processor 905 to perform the features of the computer system. Accordingly, such computer programs represent controllers of the computer system.

Computer System 960 also communicates with card reader 720 for reading identification or credit/debit card information from a user or patient and a strip reader 410 for optically reading the results on a test strip.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 10:
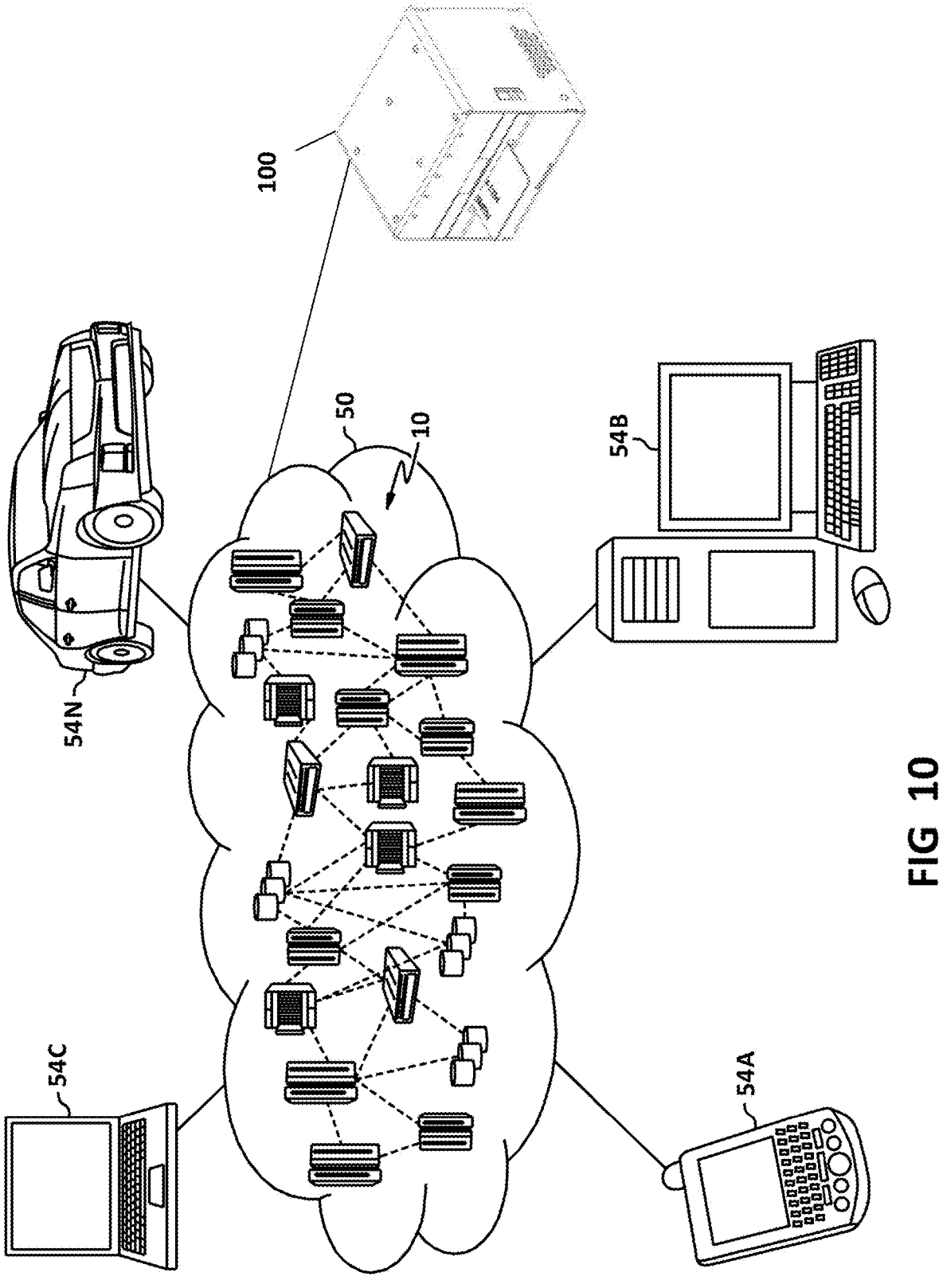
FIG. 10 depicts an environment for using a system in accordance with an embodiment of the present invention.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, testing device 100 and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N and 100 shown in FIG. 1 are intended to be illustrative only and that computing nodes 10 and cloud computing environment 50 can communicate with any type of computerized device over any type of network and/or network addressable connection (e.g., using a web browser).

Figure 11:
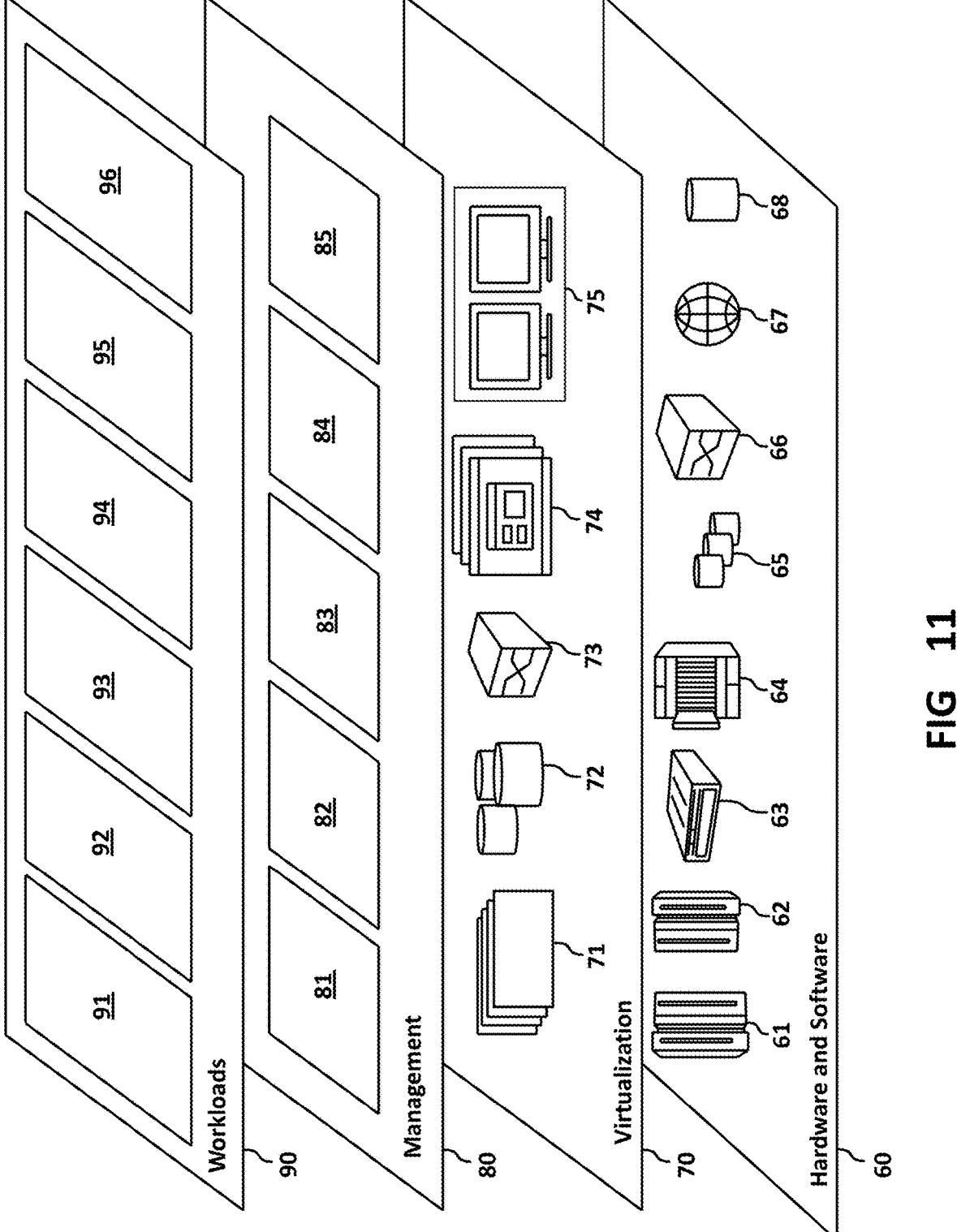
FIG. 11 depicts a high-level block diagram computer system, which can be used to implement one or more aspects of the present invention.

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65 storing test databases and results databases; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: data mining of test databases and results databases 91; software development and lifecycle management 92; machine learning of test strip analysis 93; headless testing device communications and control 94; computer (non-headless) communication and control 95; and testing analysis 96.

Figure 12:
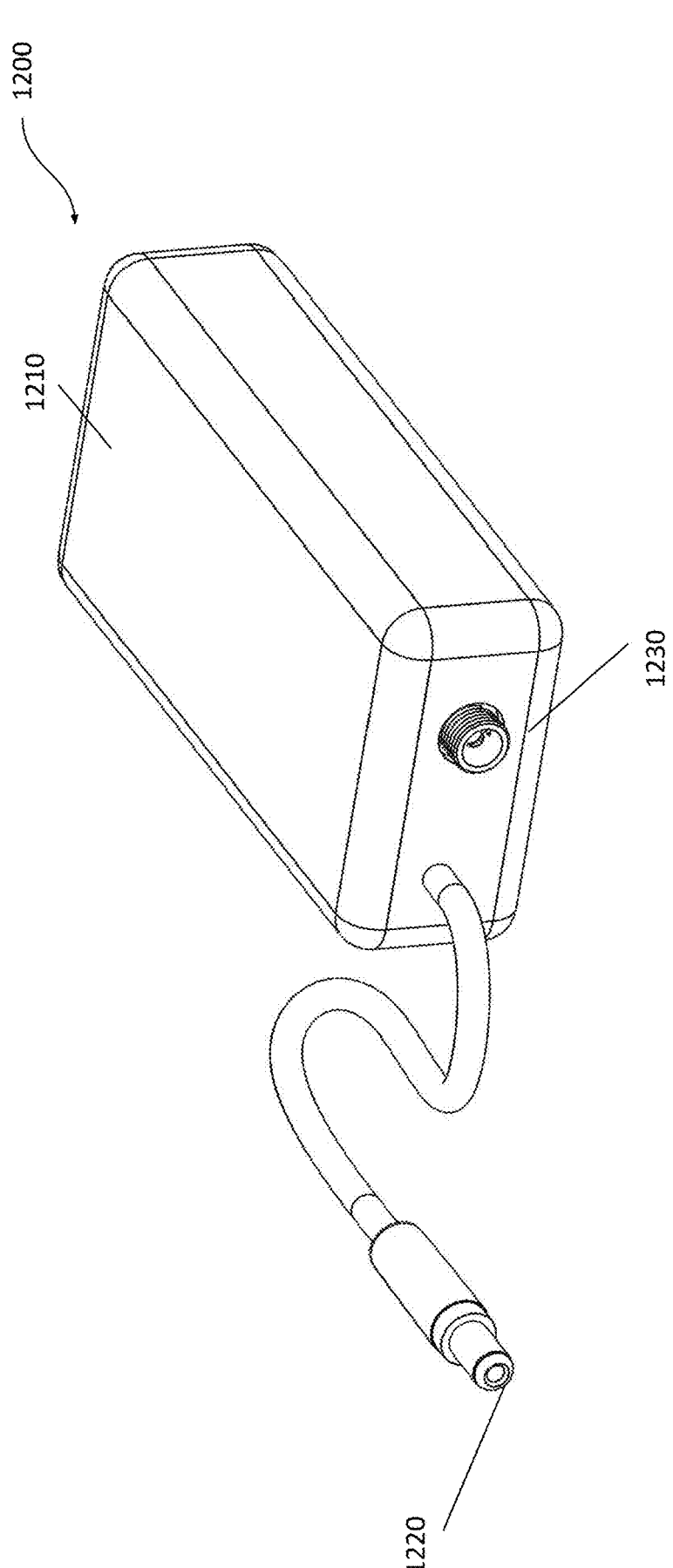
FIG. 12 depicts an orthogonal view of a battery pack for the testing device according to an embodiment of the present invention.

FIG. 12 depicts an orthogonal view of a battery pack 1200 for the testing device 100 according to an embodiment of the present invention. Battery pack 1200 includes an encased battery 1210 having a power input port 1230 for accepting a DC power supply and an output port 1220 for plugging in to a power input port of the testing device 100. By using battery pack 1200, testing device 100 may be used without needing an AC power source present.

Figure 13:
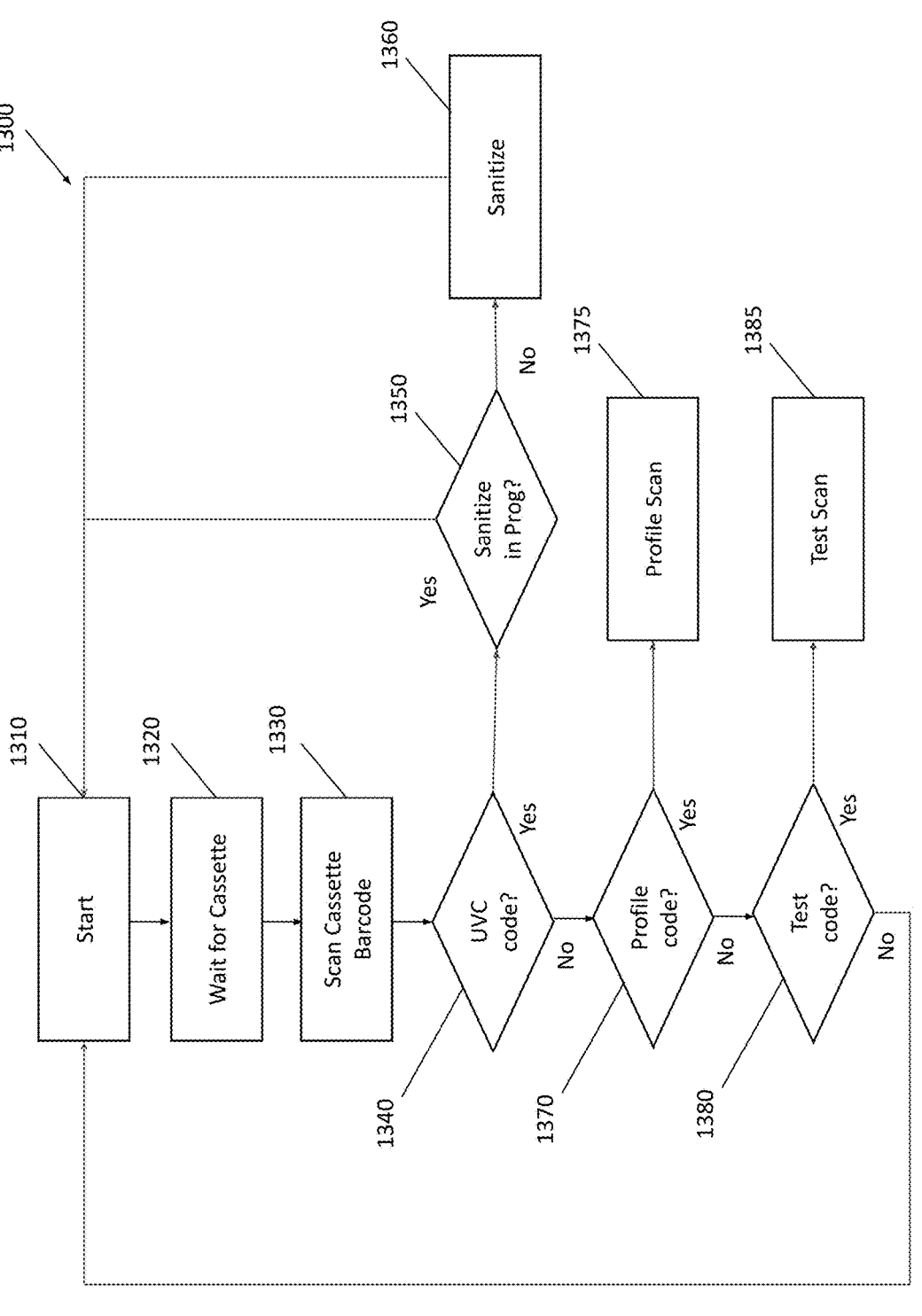
FIG. 13 depicts a flowchart of a method for reading a test strip and sterilization process in a clear assay or sample carrier and providing a result in accordance with an embodiment of the present invention.

FIG. 13 depicts a flowchart 1300 of a method for reading a test strip and sterilization process in a clear assay or sample carrier and providing a result in accordance with an embodiment of the present invention. The method starts (block 1310) and waits for the detection of a clear assay, cassette, or card (block 1320). The method uses an imaging source, such as, for example, a camera, data file or files, xerography device, video feed, data stream, or other source of image information, to detect visual features, such a visual feature may be the shape of the inserted cassette, text on the cassette, presence or absence of one or more barcodes, data matrices or QR codes, or one or more colors present on the cassette, for example. In an alternative embodiment, the method may use a mechanical switch to detect the presence of a clear assay, cassette, or card. If there is no clear assay, cassette, or card, the method waits in a loop that may be, for example, 1 second long, until the detection of the clear assay, cassette, or card.

The method scans a visual feature off of the clear assay, cassette, or card to identify a test that is being conducted and optionally a patient (block 1330). Any reference to cassette herein also incorporates the use of a clear assay. Embodiments of the invention may use a visual feature, such as text, a shape of the cassette, or identifiers of the cassette to determine the test being conducted. A visual feature may also be a barcode, QR code, or data matrix. For example, a COVID test may be being performed, but other tests as previously described, such as a seasonal flu test may be being performed. The method uses the visual feature to determine the test being conducted regardless of the alignment of the cassette with respect to the carrier. Alignment may include orientation of the cassette. In other words, regardless of orientation or alignment of the cassette, the visual feature is analyzed to determine the test being conducted.

In the case of a data matrix as the visual feature, information within the data matrix identifies a unique cassette identifier, a manufacturer code definition, supplier code definition, a profile code that together determine a test configuration profile to be used for this test. For other visual features, such as QR code, barcode, text, a shape of the cassette, identifiers of the cassette, or combinations thereof, in determining the test being conducted, the visual feature may initially be used to identify the test vendor. Once the test vendor is identified, if necessary, the specific test from that vendor is determined. Following identification of the vendor and specific test, the test configuration profile is determined.

The method checks to determine if the visual feature present in the view of the imaging device is a UVC code (block 1340). If so, a check is made to see if a sanitization process is already in progress or has completed within a predetermined time frame, for example, five minutes (block 1350). If not, sanitization begins by, for example, turning on a UVC light source for a predetermined period of time, for example, 30 seconds. In an alternative embodiment, ionizing radiation may be used to perform the sterilization. The UVC code of the visual feature specifies the predetermined period of time to sanitize, for example, 30 seconds. Movement in the field of vision of the imaging device may halt sterilization and trigger an alert. Successful or failed sanitization results may be uploaded to a central database. After initiating sanitization, the method returns to block 1310. Furthermore, if sanitization is occurring or has recently occurred (block 1350), the method returns to block 1310.

Figure 14:
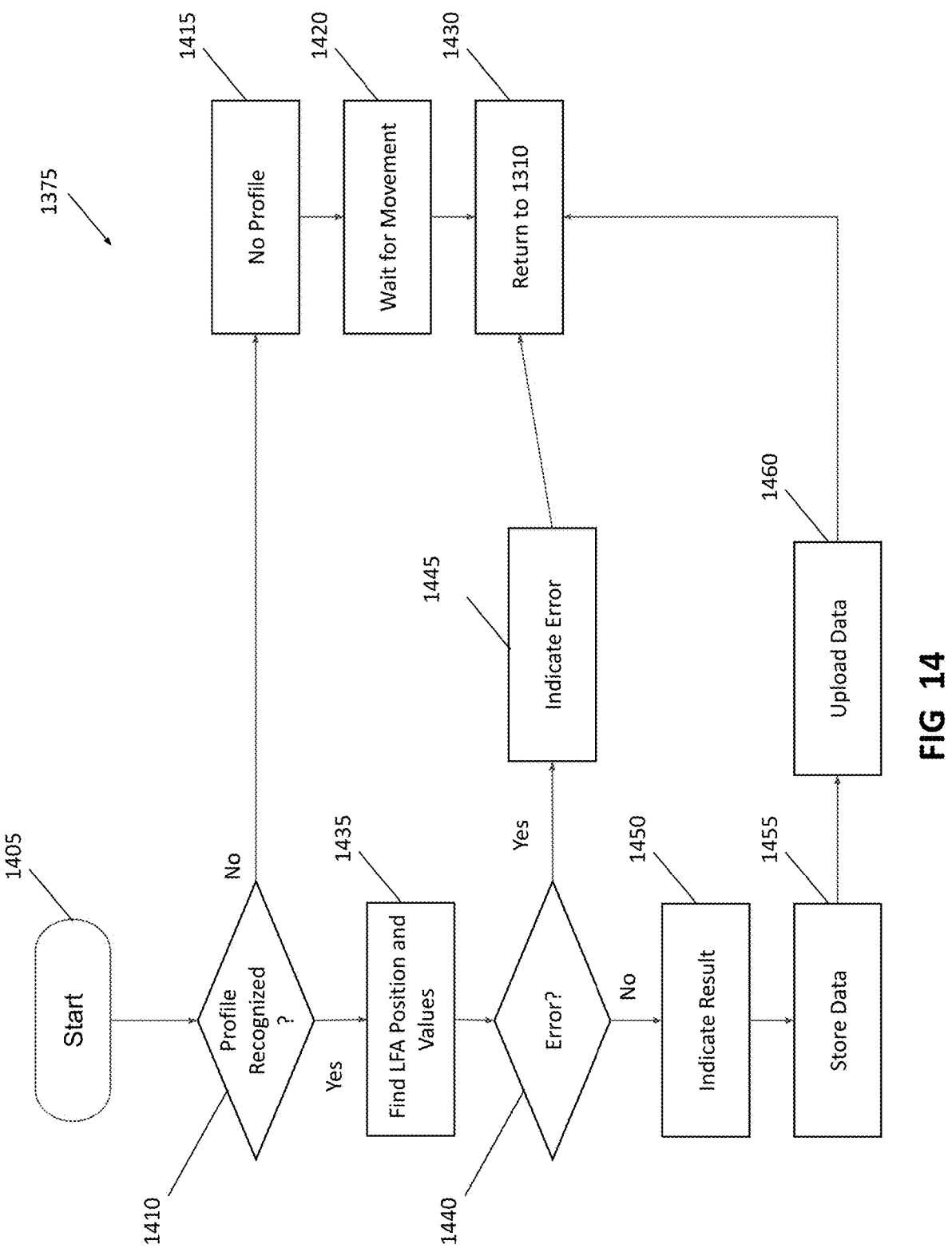
FIG. 14 depicts a flowchart of a method for performing a profile scan in accordance with an embodiment of the present invention.

If the visual feature is a profile code that indicates the presence of an actual test cassette (block 1370), a profile scan is made to determine test results for that test cassette (block 1375) (explained in further detail in FIG. 14). If the visual feature is a functional test profile code that indicates the presence of a functional test cassette (block 1380), a functional test cassette scan is made to test the test system 100 (block 1385) (explained in further detail in FIG. 15). Control then returns to block 1310.

FIG. 14 depicts a flowchart of a method 1375 for performing a profile scan in accordance with an embodiment of the present invention. A check is made to determine if a test configuration profile associated with the profile code on the visual feature is present in a local database (block 1410). Test configuration profiles and equivalence curves are stored locally in, for example, an XML or JSON file. Each XML or JSON file may contain multiple test configuration profiles with associated equivalence curves. In one embodiment of the invention, if the test configuration profile is not present in the local database, a fetch may be made to pull the appropriate test configuration file from a central test database for storage in the local database. Thus, new tests that are used in the field will cause the local database to update itself with information from the remote database.

In a second embodiment of the invention, if no profile is present (block 1410), a profile error is returned (block 1415), the method waits until there is movement caught by the imaging device (block 1420), and then flow returns to block 1310 (block 1430).

If the test configuration profile is present in the local database (block 1410), the LFA position and values are determined (block 1435) based on the imaging source. The imaging source is, for example, a camera, data file or files, xerography device, video feed, data stream, or other source of image information. To scan the LFA strip, the configuration file corresponding to the profile number provides brightness settings for LEDs that provide light at various wavelengths that will shine upon the LFA strip. The LEDs are turned on to that appropriate brightness level, and after a delay to permit the LEDs to arrive at the proper brightness and a camera to stabilize to take an image at that brightness level, images are taken by the camera. The number of images taken is indicated by the configuration file associated with the configuration profile. The areas of the LFA strip indicated by the profile to contain control and test lines are analyzed for color and intensity and results are averaged between several images taken to determine numerical values to be presented as results of the LFA strip scan.

Intensity of the test lines and control lines are calculated as follows. Each of the plurality of images is straightened as carriers can be inserted askew, the area around the test lines and control lines is selected, and the intensity of the image is intensity normalized so that the blank part of the paper is set to zero. Please note that the intensity values of 0-255 are inverted in that pure white is 0 and pure black is 255. The rectangular area of both the test lines and the control lines are found, and typically may be between 3 and 10 pixels width of lines depending on the test kit manufacturer. The median intensity lines within the lines are then averaged together by summing the intensity values of each pixel comprising both median lines and averaging the pixel intensity to determine an intensity of each of the test lines and control lines.

If the scan of the LFA strip is bad for any reason (block 1440), an error result is indicated (block 1445) and the result indicating a fault may be uploaded to a central database in association with the patient's unique ID with control returning block 1310 (block 1430).

If the scan of the LFA strip is good (block 1440), the LFA scan is compared to the associated test configuration profile to determine an LFA test result. The test result is indicated (positive/negative/error) (block 1450), and the actual value data of each test is stored (block 1455) and sent back to the central patient database (block 1460) so that a graph can be plotted for tests taken of a patient over time to see the magnitude of viral load or antibody concentration over time.

Also, mathematical models may be used to develop data across large data sets of patients to see for example efficacy of a vaccine as a function of IgG/IgM concentration from samples taken over time across a cohort of patients. Patient information that identifies a specific person, such as a social security number or national ID number, may optionally not be stored in the central patient database, with only demographic data retained. Flow then goes to block 1430 where it returns to block 1310.

Figure 15:
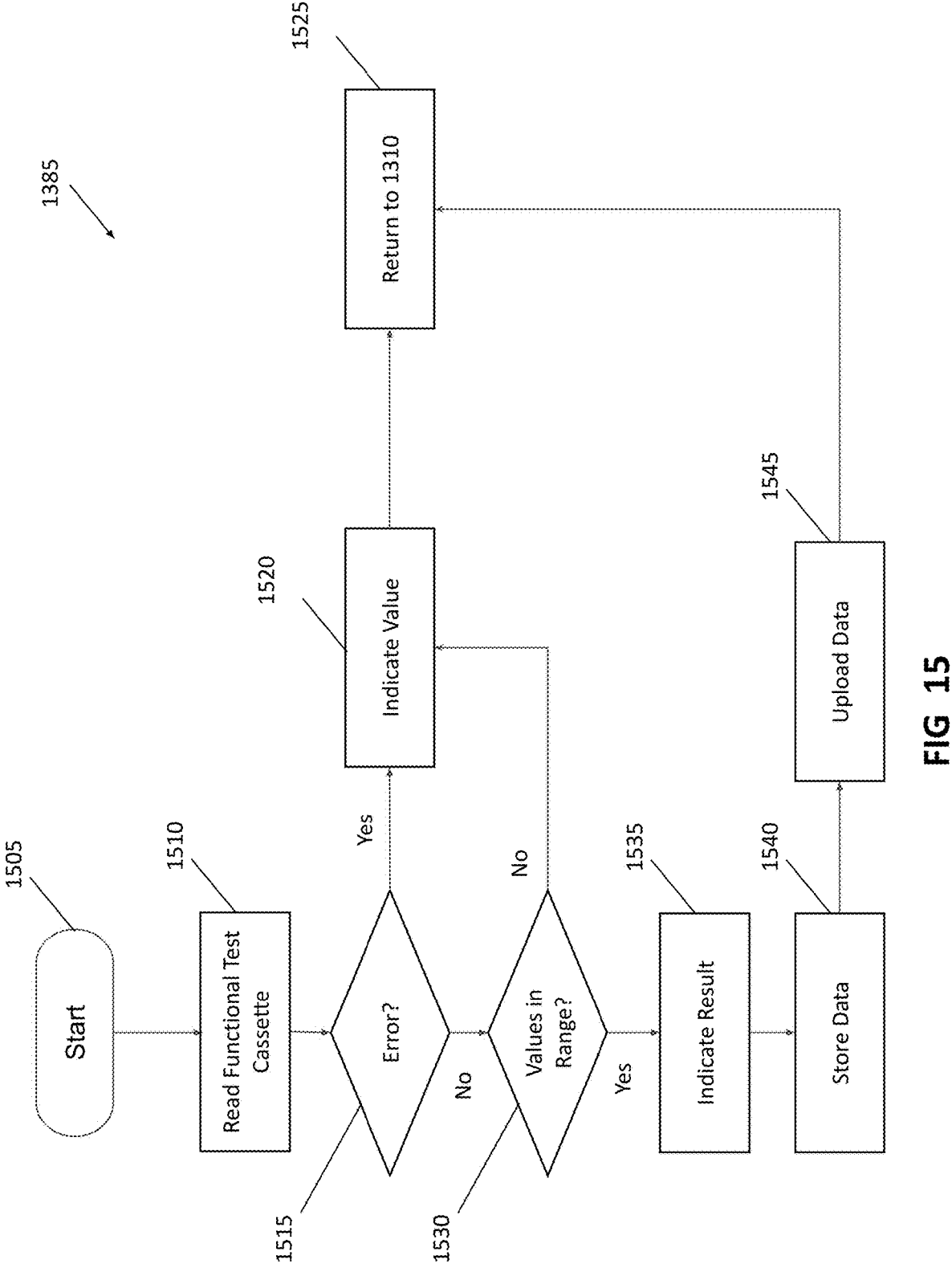
FIG. 15 depicts a flowchart of a method for performing a functional test scan in accordance with an embodiment of the present invention.

FIG. 15 depicts a flowchart of a method 1385 for performing a functional test scan in accordance with an embodiment of the present invention. The functional test cassette's purpose is to test the test system with a cassette having an LFA with a known result that should be determined upon testing. When the process starts (block 1505), the functional test cassette is scanned (block 1510) using the methodology previously discussed with respect to block 1435. If the scan of the LFA strip is bad for any reason (block 1515), an error result with a value is indicated (block 1520) with control returning block 1310 (block 1430).

If the values read from the functional test cassette are not within expected range (block 1530), the method goes to block 1520 where the error result is indicated.

If the values read from the functional test cassette are within expected value, the result is indicated (block 1535), the data is stored locally regarding the result (block 1540), and also uploaded to the central database (block 1545). The method then returns to block 1525.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Go (golang), Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A testing system, comprising:
a processor;
memory coupled to the processor;
a lateral flow assay ("LFA") strip reader coupled to the processor for reading an LFA strip in a cassette;
an LFA strip image created by the LFA strip reader, where the LFA strip image further comprises an image of at least part of the cassette;
the processor further configured to initiate a sterilization process of an interior of the testing system when the LFA strip image includes a visual feature located on the cassette, an existence of the visual feature located on the cassette indicating that the sterilization process should be triggered, and the visual feature not comprising an identification of the LFA strip, and the visual feature comprising a code indicating a sterilization trigger, wherein the code indicating the sterilization trigger comprises one of a QR code, a data matrix, or a bar code.

2. The system of claim 1, wherein the LFA strip reader is an imaging device.

3. The system of claim 2, wherein the sterilization process is halted when the imaging device detects movement.

4. The system of claim 1, wherein a message is transmitted by a communications interface in communication with the processor to a central database when the sterilization process is halted.

5. The system of claim 1, wherein the LFA strip reader comprises a plurality of LED lights activated based on a test configuration profile and a camera for reading the LFA strip and generating the LFA strip image.

6. The system of claim 5 wherein the plurality of LED lights includes visible lights and ultraviolet UVC lights, and wherein the sterilization trigger causes the processor to turn on the UVC lights.

7. The system of claim 6, further comprising an ultraviolet filter placed in front of an image sensor in the LFA strip reader to protect the image sensor from UVC lights during the sterilization.

8. The system of claim 7, wherein a length of time that the UVC lights are turned on is based on information in the visual feature.

9. The system of claim 1, wherein the visual feature comprises text on the cassette and a color on the cassette.

10. A method, comprising:
   reading a lateral flow assay ("LFA") strip in a cassette, using an imaging device, to generate an LFA strip image, where the LFA strip image further comprises an image of at least part of the cassette and wherein the LFA strip image comprises a visual feature;
   providing the LFA strip image to a processor;
   activating, using the processor, a sterilization process when the LFA strip image contains a visual feature comprising a code to trigger the sterilization process and the visual feature not comprising an identification of the LFA strip, the sterilization process to sterilize an interior of a testing machine.

11. The method of claim 10, wherein the activating the sterilization process using the processor comprises activating a UVC light.

12. The method of claim 11, the UVC light is activated for a predetermined period of time.

13. The method of claim 12, wherein the predetermined period of time is based on data within the visual feature.

14. The method of claim 10, wherein the sterilization process is halted when movement is detected in the LFA strip image.

15. The method of claim 10, further comprising transmitting an alert to a central database when the sterilization process is halted.

16. The method of claim 10, further comprising logging a successful completion of the sterilization process in a central database.

17. The method of claim 10, further comprising interrupting the sterilization process upon the processor receiving a request to interrupt the sterilization process.

18. A system, comprising:
   a carrier to receive a lateral flow assay ("LFA") for processing;
   an LFA strip reader for obtaining an LFA strip image in the carrier;
   a processor to analyze the LFA strip image, and identify a visual feature comprising one of: a shape of a cassette containing an LFA strip, text on the cassette, a barcode on the cassette, a color on the cassette, a bar code on a surface of a receptacle into which the cassette is inserted that is covered up by the cassette, the visual feature indicating a sterilization trigger, and wherein the visual feature does not indicate an identification of the LFA strip; and
   the processor to initiate a sterilization process of the carrier in response to identifying the visual feature.

19. The system of claim 18, wherein the LFA strip reader comprises a plurality of light emitting diode (LED) lights and a camera.

20. The system of claim 19, wherein the sterilization process uses an ultraviolet C (UVC) light to sterilize the carrier.

21. The system of claim 19, further comprising:
   an ultraviolet filter in front of the camera, to protect the camera from ultraviolet light.

22. The system of claim 18, further comprising:
   a communication interface to transmit a result of the sterilization process to a server.

23. The system of claim 1, wherein the visual feature further specifies a predetermined period of time to sterilize the interior of the testing system.

24. The method of claim 10, wherein the visual feature further specifies a predetermined period of time to sterilize the interior of the testing machine.

25. The system of claim 18, wherein the visual feature further specifies a predetermined period of time to sterilize the carrier.

26. The system of claim 1, wherein the cassette comprises a clear assay.

* * * * *